United States Patent
Kataoka et al.

(10) Patent No.: US 9,808,480 B2
(45) Date of Patent: Nov. 7, 2017

(54) UNIT STRUCTURE-TYPE PHARMACEUTICAL COMPOSITION FOR NUCLEIC ACID DELIVERY

(71) Applicants: THE UNIVERSITY OF TOKYO, Tokyo (JP); NanoCarrier Co., Ltd., Kashiwa-shi (JP)

(72) Inventors: Kazunori Kataoka, Tokyo (JP); Kanjiro Miyata, Tokyo (JP); Nobuhiro Nishiyama, Tokyo (JP); Kensuke Osada, Tokyo (JP); Sumiyo Watanabe, Tokyo (JP); Shigeto Fukushima, Tokyo (JP); Hiroyuki Chaya, Tokyo (JP); Hiroyasu Takemoto, Tokyo (JP); Yasuki Kato, Kashiwa (JP)

(73) Assignees: NANOCARRIER CO., LTD., Kashiwa-shi (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/395,745

(22) PCT Filed: Apr. 30, 2013

(86) PCT No.: PCT/JP2013/062531
§ 371 (c)(1),
(2) Date: Oct. 20, 2014

(87) PCT Pub. No.: WO2013/162041
PCT Pub. Date: Oct. 31, 2013

(65) Prior Publication Data
US 2015/0080454 A1 Mar. 19, 2015

(30) Foreign Application Priority Data
Apr. 27, 2012 (JP) .................................. 2012-102841

(51) Int. Cl.
*C12N 15/11* (2006.01)
*A61K 31/713* (2006.01)
*A61K 9/00* (2006.01)
*A61K 47/48* (2006.01)

(52) U.S. Cl.
CPC .......... *A61K 31/713* (2013.01); *A61K 9/0019* (2013.01); *A61K 47/48215* (2013.01); *A61K 47/48315* (2013.01)

(58) Field of Classification Search
CPC .............. A61K 38/00; A61K 47/48323; A61K 31/712; A61K 31/31713; A61K 47/48246; C12N 15/11; C12N 15/113
See application file for complete search history.

(56) References Cited

U.S. PATENT DOCUMENTS

| 7,642,343 | B2 | 1/2010 | Nagasaki et al. |
| 7,780,957 | B2 | 8/2010 | Kataoka et al. |
| 8,318,205 | B2 | 11/2012 | Kataoka et al. |
| 8,431,545 | B2 | 4/2013 | Kataoka et al. |
| 8,546,487 | B2 | 10/2013 | Kataoka et al. |
| 8,592,385 | B2 | 11/2013 | Kataoka et al. |
| 8,668,933 | B2 | 3/2014 | Hori et al. |
| 8,791,086 | B2 | 7/2014 | Kataoka et al. |
| 8,822,213 | B2 | 9/2014 | Stayton et al. |
| 8,853,167 | B2 | 10/2014 | Kato et al. |
| 9,114,177 | B2 | 8/2015 | Kataoka et al. |
| 2002/0016304 | A1* | 2/2002 | Maruyama et al. ............ 514/44 |
| 2003/0148929 | A1 | 8/2003 | Goto et al. |
| 2005/0260651 | A1* | 11/2005 | Calias .............. A61K 47/48215 435/6.11 |
| 2008/0249049 | A1* | 10/2008 | Kataoka et al. ................. 514/44 |
| 2008/0305116 | A1 | 12/2008 | Van Vlijmen et al. |
| 2010/0121043 | A1* | 5/2010 | Kataoka et al. ............. 536/24.5 |
| 2010/0221320 | A1 | 9/2010 | Kato et al. |
| 2011/0052917 | A1 | 3/2011 | Kataoka et al. |
| 2011/0123636 | A1 | 5/2011 | Stayton et al. |
| 2011/0129921 | A1 | 6/2011 | Johnson et al. |
| 2011/0142951 | A1 | 6/2011 | Johnson et al. |

(Continued)

FOREIGN PATENT DOCUMENTS

| EP | 2415871 A | 2/2012 |
| JP | 2000210079 | 8/2000 |

(Continued)

OTHER PUBLICATIONS

DeRouchey et al, Monomolecular assembly of siRNA and poly-(ethylene glycol)-peptide copolymers, 2008, Biomacromolecules, vol. 9, pp. 724-732.* effect of polyelectrolyte complexes on cellular uptake and gene silencing efficiency, 2011, Macromolecular Bioscience, vol. 11, pp. 410-418.*

Nojima et al., Lactoferrin conjugated with 40-kDa branched poly-(ethylene glycol) has an improved circulating half-life, 2009, Pharmaceutical Research, vol. 26, pp. 2125-2132.*

Kano et al., Grafting of poly(ethylene glycol) to poly-lysine augments its lifetime in blood circulation and accumulation in tumors without loss of the ability to associated with siRNA, 2011, Journal of Controlled Release, vol. 149, pp. 2-7.*

Shimizu, H. et al, siRNA-Based Therapy Ameliorates Glomerulonephritis, J Am Soc Nephrol, 2010, vol. 21, No. 4, p. 622-633.

(Continued)

*Primary Examiner* — Dana Shin
(74) *Attorney, Agent, or Firm* — J-Tek Law PLLC; Jeffrey D. Tekanic; Scott T. Wakeman

(57) ABSTRACT

A unit structure-type pharmaceutical composition includes at least one nucleic acid, such as siRNA, electrostatically bound to at least one block copolymer having a cationic polyamino acid segment and a hydrophilic polymer chain segment. The negative charge(s) of the nucleic acid are counterbalanced, at least substantially, by the positive charge(s) of the cationic polyamino acid segment such that the pharmaceutical composition is electrically neutral or nearly electrically neutral. Further, the nucleic acid is covered with the hydrophilic polymer chain segment(s). The at least one block copolymer thereby improves the blood retention capability of the nucleic acid(s).

16 Claims, 10 Drawing Sheets

(56) References Cited

U.S. PATENT DOCUMENTS

| | | | |
|---|---|---|---|
| 2011/0143434 A1 | 6/2011 | Stayton et al. | |
| 2011/0143435 A1 | 6/2011 | Stayton et al. | |
| 2011/0144017 A1* | 6/2011 | Dorwald | A61K 47/48215 514/11.4 |
| 2011/0281354 A1 | 11/2011 | Stayton et al. | |
| 2011/0281934 A1 | 11/2011 | Johnson et al. | |
| 2011/0286957 A1 | 11/2011 | Prieve et al. | |
| 2012/0014975 A1* | 1/2012 | Hegen | A61K 47/48215 424/179.1 |
| 2012/0021514 A1 | 1/2012 | Johnson et al. | |
| 2012/0053295 A1 | 3/2012 | Kataoka et al. | |
| 2012/0076836 A1 | 3/2012 | Hori et al. | |
| 2012/0076866 A1 | 3/2012 | Ishii et al. | |
| 2012/0093881 A1 | 4/2012 | Kato et al. | |
| 2012/0149649 A1 | 6/2012 | Kato et al. | |
| 2014/0017328 A1 | 1/2014 | Kataoka et al. | |
| 2014/0228516 A1 | 8/2014 | Stayton et al. | |

FOREIGN PATENT DOCUMENTS

| | | | |
|---|---|---|---|
| JP | 2008511290 | A | 4/2008 |
| JP | 2011162512 | | 8/2011 |
| JP | 2010233499 | A | 10/2011 |
| JP | 2012500793 | A | 1/2012 |
| WO | 2005078084 | A1 | 8/2005 |
| WO | 2010021770 | A1 | 2/2010 |
| WO | 2010114013 | A1 | 10/2010 |
| WO | 2009113645 | | 11/2010 |
| WO | 2012096399 | A1 | 7/2012 |

OTHER PUBLICATIONS

Lee et al., Di- and triblock siRNA-PEG copolymers: PEG density Communication from European Patent Office for counterpart EP application No. 13 782 198.9 dated Nov. 30, 2015, including Search Opinion, Supplementary European Search Report and examined claims 1-9.
English translation of Written Opinion for parent application No. PCT/JP2013/062531.
English translation of International Search Report for parent application No. PCT/JP2013/062531.
Kim et al., Precise Engineering of siRNA Delivery Vehicles to Tumors Using Polyion Complexes and Gold Nanoparticles, ACS NANO, vol. 8, No. 9, 2014, pp. 8979-8991.
U.S. Appl. No. 13/808,237.
U.S. Appl. No. 14/358,816.
U.S. Appl. No. 13/979,546.
Suma et al., Enhanced stability and gene silencing ability of siRNA-loaded polyion complexes formulated from polyaspartamide derivatives with a repetitive array of amino groups in the side chain, Biomaterials 33, pp. 2770-2779 (2012).
Zhao et al., N/P Ratio Significantly Influences the Transfection Efficiency and Cytotoxicity of a Polyethylenimine/Chitosan/DNA Complex, Biol. Pharm. Bull. 32(4) pp. 706-710 (2009).
Office Action from the Japanese Patent Office dated Mar. 29, 2017 in counterpart Japanese application No. 2014-512733, and translation thereof.

* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: sense strand of siRNA for luciferase including
      dT terminus

<400> SEQUENCE: 1
cuuacgcuga guacuucgat t                                                  21

<210> SEQ ID NO 2
<211> LENGTH: 21
<212> TYPE: DNA
<213> ORGANISM: Artificial
<220> FEATURE:
<223> OTHER INFORMATION: antisense strand of siRNA for luciferase
      including dT terminus

<400> SEQUENCE: 2
ucgaaguacu cagcguaagt t                                                  21

<210> SEQ ID NO 3
<211> LENGTH: 21
<212> TYPE: DNA
<213> ORGANISM: Artificial
<220> FEATURE:
<223> OTHER INFORMATION: sense strand of siRNA for human vascular
      endothelial growth factor including dT terminus

<400> SEQUENCE: 3
gaucucauca ggguacucct t                                                  21

<210> SEQ ID NO 4
<211> LENGTH: 21
<212> TYPE: DNA
<213> ORGANISM: Artificial
<220> FEATURE:
<223> OTHER INFORMATION: antisense strand of siRNA for human vascular
``` endothelial growth factor including dT terminus

```
<400> SEQUENCE: 4
ggaguacccu gaugagauct t                                              21

<210> SEQ ID NO 5
<211> LENGTH: 21
<212> TYPE: RNA
<213> ORGANISM: Artificial
<220> FEATURE:
<223> OTHER INFORMATION: sense strand of siRNA for polo-like kinase 1
<220> FEATURE:
<221> NAME/KEY: um
<222> LOCATION: (4)..(4)
<220> FEATURE:
<221> NAME/KEY: um
<222> LOCATION: (10)..(10)
<220> FEATURE:
<221> NAME/KEY: um
<222> LOCATION: (14)..(14)
<220> FEATURE:
<221> NAME/KEY: um
<222> LOCATION: (18)..(18)

<400> SEQUENCE: 5
agaucacccu ccuuaaauau u                                              21

<210> SEQ ID NO 6
<211> LENGTH: 21
<212> TYPE: RNA
<213> ORGANISM: Artificial
<220> FEATURE:
<223> OTHER INFORMATION: antisense strand of siRNA for polo-like kinase
      1
<220> FEATURE:
<221> NAME/KEY: gm
<222> LOCATION: (8)..(8)
<220> FEATURE:
<221> NAME/KEY: um
<222> LOCATION: (17)..(17)

<400> SEQUENCE: 6
uauuuaagga gggugaucuu u                                              21
```

UNIT STRUCTURE-TYPE PHARMACEUTICAL COMPOSITION FOR NUCLEIC ACID DELIVERY

CROSS-REFERENCE

This application is the US national stage of International Patent Application No. PCT/JP2013/062531 filed on Apr. 30, 2013, which claims priority to Japanese Patent Application No. 2012-102841 filed on Apr. 27, 2012.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| NCC007_seq.txt | Oct. 20, 2014 | 2 |

TECHNICAL FIELD

The present invention relates to a unit structure-type pharmaceutical composition including a nucleic acid and a block copolymer. The unit structure-type pharmaceutical composition or a pharmaceutical preparation including the composition is hereinafter sometimes abbreviated as "unit structure".

BACKGROUND ART

The application of siRNA to medical treatments is increasingly expected because siRNA can knock down target mRNA specifically and effectively. The development of an effective delivery system is indispensable to applying siRNA to medical treatments. In recent years, it has been clarified in clinical trials that the therapeutic effect on age-related macular degeneration (CNV) by intraocular administration of naked siRNA does not result from a sequence-specific gene knockdown effect mediated by siRNA, but rather results from a non-sequence-specific effect via recognition by the cell surface Toll-like receptor-3 (TLR-3); thus, the development of a carrier, which is stable outside of cells and is capable of accurately delivering siRNA into the cells in any in vivo application of siRNA, is considered to be important.

Cationic polymers have been provided as carriers that introduce nucleic acid into eukaryotic cells by forming a complex with a small-molecule nucleic acid such as siRNA under physiological conditions and cause the nucleic acid to be expressed (for example, Patent Literature 1). In case nucleic acid such as siRNA will be applied to medical treatments, the nucleic acid preferably has a high blood retentivity from the viewpoint of sustaining the effect, and there is still room for improvement in the blood retention capabilities of conventional cationic polymers.

CITATION LIST

Patent Literature

Patent Literature 1: JP 2010-233499 A

SUMMARY OF THE INVENTION

A main object of the present invention is the improvement of the blood retention capabilities of a nucleic acid in a cationic polymer-type carrier.

According to the present invention, a unit structure-type pharmaceutical composition (a unit structure) is provided. The unit structure contains a block copolymer, which has a cationic polyamino acid segment and a hydrophilic polymer chain segment, and a nucleic acid; the unit structure is electrically neutral by counterbalancing the negative charge(s) of the nucleic acid with the positive charge(s) of the cationic polyamino acid segment and the nucleic acid is covered with the hydrophilic polymer chain segment.

According to another aspect of the present invention, a pharmaceutical preparation containing the unit structure-type pharmaceutical composition is provided.

Furthermore, according to another aspect of the present invention, a block copolymer that can form the unit structure-type pharmaceutical composition is provided. The block copolymer has a cationic polyamino acid segment and a hydrophilic polymer chain segment; the cationic polyamino acid segment is electrically neutral by counterbalancing the negative charge(s) of the nucleic acid with the positive charge(s) of the cationic polyamino acid segment and the hydrophilic polymer chain segment has a chain length that covers the nucleic acid.

According to the present invention, it is possible to improve the blood retention capabilities of a nucleic acid in a cationic polymer-type carrier. According to the present invention, it is possible to dramatically improve anti-tumor effects as compared to conventional carriers for nucleic acid delivery.

DETAILED DESCRIPTION OF THE EMBODIMENTS

<A. Unit Structure>

Figure 1A:
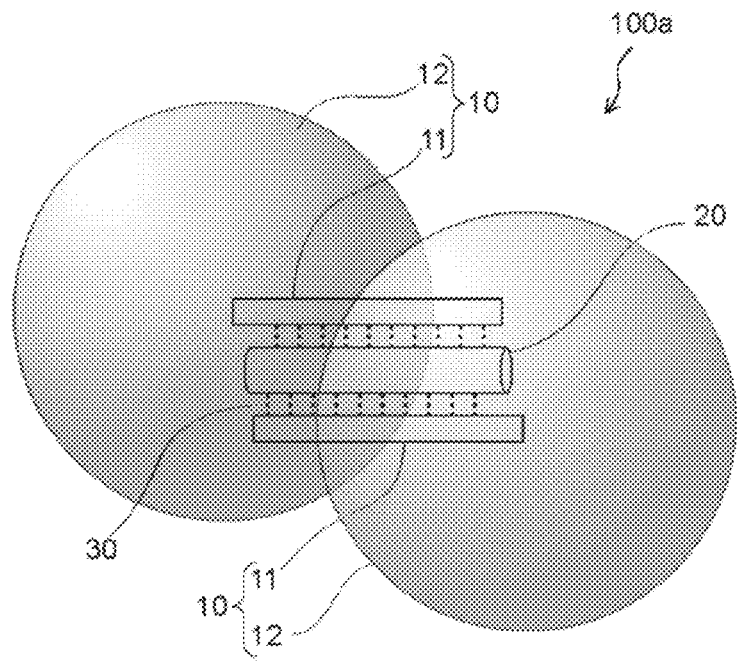
FIG. 1 are schematic views that explain a presumed structure of a unit structure in one exemplary embodiment of the present invention.

A unit structure of the present invention includes: a block copolymer, which has a cationic polyamino acid segment and a hydrophilic polymer chain segment, and a nucleic acid; the unit structure is electrically neutral by counterbalancing the negative charge(s) of the nucleic acid with the positive charge(s) of the cationic polyamino acid segment, and the nucleic acid is covered with the hydrophilic polymer chain segment. In this manner, by adjusting the relationship between the charge number of the cationic polyamino acid segment and the charge number of the nucleic acid and by covering the nucleic acid with the hydrophilic polymer chain segment, the blood retention capabilities of the nucleic acid in a cationic polymer-type carrier can be significantly improved, because it is possible to prevent metabolism or decomposition of the nucleic acid caused by electrical charge-based attraction and physical (charge-independent) proximity to proteins and enzymes in the blood.

In the present specification, the state "the unit structure is electrically neutral" does not exclude a state in which the difference between the total of the charges derived from the cationic group(s) of the cationic polyamino acid segment and the total of the charges derived from the nucleic acid in the unit structure falls within the range of about ±10%, more strictly the range of about ±5%. For example, in case the charge total of the nucleic acid is 40, the states are not excluded in which the charge total derived from the cationic groups in the unit structure falls within the range of from 36 to 44, strictly the range of from 38 to 42, more strictly the range of from 39 to 41. It should be noted that, in the block copolymer used in the present invention, the hydrophilic polymer chain segment and the cationic polyamino acid segment may each exhibit a certain degree of polydispersity. Therefore, in the present specification, when referring to the properties (such as molecular weight, polymerization degree, and radius of inertia) of the block copolymer, it refers to the average of all polymers exhibiting polydispersity, unless otherwise specified. Therefore, the charge number is calculated based on the polymerization degree, which is defined as the average polymerization degree that was obtained by actual measurement. For example, the polymerization degree of polylysine can be measured by the method that will be described below in the Examples.

In the present specification, the state "the nucleic acid is covered with a hydrophilic polymer chain segment" means a state in which the entirety of the nucleic acid is covered with the hydrophilic polymer chain segment(s). More specifically, it means the state in which the entirety of the nucleic acid is enclosed within the spatial extent (radius of inertia) of the hydrophilic polymer chain segment. In case the unit structure is formed by a plurality of block copolymers, the hydrophilic polymer chain segment of a single block copolymer is not required to cover the entirety of the nucleic acid; the entirety of the nucleic acid may be enclosed within the comprehensive spatial extent derived from the hydrophilic polymer chain segments of each block copolymer.

Figure 1B:
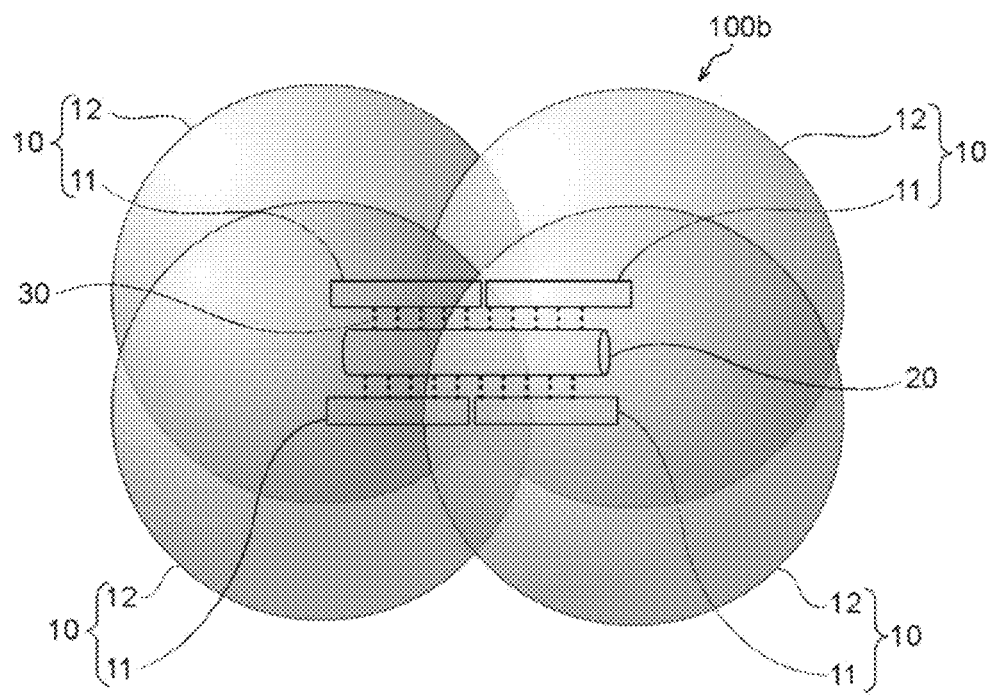

FIGS. 1(a) and 1(b) are schematic views that respectively explain the presumed structure of a unit structure in one exemplary embodiment of the present invention. Without limiting the present invention, in a unit structure 100a or 100b of the present invention, it is presumed that cationic polyamino acid segments 11 of the block copolymers 10 are arranged along a nucleic acid 20 and form electrostatic bonds 30 with the nucleic acid 20; hydrophilic polymer chain segments spatially extend to cover the nucleic acid 20 (in the Figures, the spheres represented by reference symbol 12 represent the spatial extents of the hydrophilic polymer chain segments). It should be noted that, although FIGS. 1(a) and 1(b) each illustrate modes in which the cationic polyamino acid segments are linearly arranged along the extension direction of the nucleic acid, the arrangement state of the cationic polyamino acid segments is not limited as long as the negative charge(s) of the nucleic acid can be offset; for example, a mode is also possible in which they are arranged to wind around and along the helical structure of the nucleic acid.

As exemplified in FIGS. 1(a) and 1(b), the unit structure of the present invention includes an unspecified large number of block copolymers and one or a plurality of nucleic acids; unlike a conventional complex (for example, a conventional nucleic acid-encapsulated core-shell polymer micelle) having a composition that is difficult to specify, one feature of the unit structure can be to include predetermined numbers of the block copolymers and the nucleic acid, which are determined based on the charge number of each. In one embodiment, the unit structure of the present invention may include (an) m×N nucleic acid(s) and (an) n×N block copolymer(s) (in this case, N is an integer of 1 or more, and m and n are each independently an integer of from 1 to 9, for example). It should be noted that, for example, the numbers of the block copolymer(s) and the nucleic acid(s) contained in the unit structure can be determined by using the method that will be described below in the Examples.

The number of the block copolymer(s) in the unit structure of the present invention is not limited as long as the block copolymer(s) can form an electrically neutral unit structure together with the nucleic acid and can cover the nucleic acid with the spatial extent of the hydrophilic polymer chain segment, and the number may be an integer of from 1 to 8, for example. In addition, the unit structure of the present invention includes, as the nucleic acid, preferably one single-stranded nucleic acid or double-stranded nucleic acid, more preferably one double-stranded nucleic acid. This is because (an) electrostatic bond(s) with the cationic polyamino acid segment(s) and encapsulation by the hydrophilic polymer chain segment(s) can be implemented in a suitable manner. As specific examples as illustrated in FIG. 1(a), the unit structure 100a of the present invention may include two of the block copolymers 10 and one nucleic acid 20. In addition, as illustrated in FIG. 1(b), the unit structure 100b of the present invention may include four of the block copolymers 10 and one nucleic acid 20. As mentioned above, the unit structure of the present invention can be formed using two or more of block copolymers. In addition, the unit structure of the present invention may be formed using one block copolymer (not shown).

<A-1. Block Copolymer>

The block copolymer capable of forming the unit structure of the present invention includes a cationic polyamino acid segment and a hydrophilic polymer chain segment. In one embodiment, the cationic polyamino acid segment has (a) positive charge(s) that offsets the negative charge(s) of the nucleic acid, which will be contained in the unit structure, and makes the unit structure electrically neutral; the hydrophilic polymer chain segment has a chain length that covers the nucleic acid. For example, the hydrophilic polymer chain segment may be arranged at the terminus (one or both termini) of the cationic polyamino acid segment. In addition, the hydrophilic polymer chain segment may be grafted onto a side chain of an intermediate portion (preferably a substantially central portion) of the cationic polyamino acid segment or may be arranged between two adjacent cationic polyamino acid segments, instead of or in addition to the terminus. In case the hydrophilic polymer chain segment is arranged between two adjacent cationic polyamino acid segments, the hydrophilic polymer chain segment is desirably arranged so as to extend in an intersecting direction to the arrangement direction of the cationic polyamino acid segments.

The block copolymer preferably includes a plurality of hydrophilic polymer chain segments (for example, one block copolymer includes two or more hydrophilic polymer chain segments). In the case of a block copolymer having a plurality of hydrophilic polymer chain segments, metabolism or decomposition by enzymes or the like can be suitably avoided because it can cover the nucleic acid more surely. As a result, a unit structure that excels more in blood retentivity can be obtained. The number of the hydrophilic polymer chain segment(s) arranged at the respective sites may be from 1 to 4, for example. A plurality of the hydrophilic polymer chain segments may be arranged in a multi-branched hydrophilic polymer structure. The number of the hydrophilic polymer chain segments arranged in the block copolymer may be 4 or more. More specifically, in case the unit structure is formed of one block copolymer, the one block copolymer may have 4 or more hydrophilic polymer chain segments (for example, the block copolymer may have two hydrophilic polymer chain segments on each of the two termini of the cationic polyamino acid segment). In addition, the block copolymer may further have a target binding site bound to the hydrophilic polymer chain side terminal, as needed. By including a target binding site, it is possible to improve the ability of the nucleic acid to arrive at the desired target site. It should be noted that, in the present specification, the block copolymer also encompasses pharmaceutically acceptable salts of the block copolymer.

As the amino acids constituting the cationic polyamino acid segment, any appropriate cationic amino acid having a cationic group (typically, an amino group, preferably a primary amino group) in the side chain can be used. Examples thereof are amino acid derivatives obtained by introducing a cationic group into a basic amino acid, such as lysine, arginine, histidine, or ornithine, or into an acidic amino acid such as aspartic acid or glutamic acid. Because the negative charge of the nucleic acid is derived from the phosphate groups, the nucleic acid has one negative charge (charge number=−1) for each one at substantially equal intervals. Therefore, from the viewpoint of suitably forming an electrostatic bond with each phosphate group in the nucleic acid, amino acids preferably may be used that have one cationic group in the side chain, more specifically an amino acid having one positive charge in the side chain at blood pH.

In the cationic polyamino acid segment, the distance between the main chain and the cationic group on the side chain is preferably short. Specifically, the cationic group is preferably bound to the main chain via preferably from 1 to 6, more preferably, from 2 to 4 atoms. This is because the blood retentivity of the unit structure (as a result, the blood retentivity of the nucleic acid) can be improved by using a block copolymer having such a side chain structure.

The cationic polyamino acid segment preferably has a positive charge in an amount substantially equal to, substantially one-half, substantially one-fourth, or substantially one-eighth of the negative charge of the nucleic acid contained in the unit structure. By providing cationic polyamino acid segments having such charge numbers, a variety of unit structures containing different numbers (for example, 1, 2, 4, or 8) of the block copolymers can be obtained.

In one preferred embodiment, the cationic polyamino acid segment has a positive charge in an amount substantially one-half of the negative charge of the nucleic acid contained in the unit structure. This is because, when amino acids having one positive charge in the side chain at blood pH constitute such a polyamino acid segment having a positive charge, a unit structure including two block copolymers relative to one nucleic acid (typically, a unit structure including one nucleic acid and two block copolymers) is formed, and the unit structure can have improved blood retentivity (as a result, blood retentivity of the nucleic acid). Although the reason for this effect is uncertain, it is conjectured that, for example, when a unit structure includes block copolymers at such a ratio, the cationic polyamino acid segment(s) readily dispose(s) over the entire length of the nucleic acid, resulting in suitably offsetting the negative charge of the nucleic acid.

The number of amino acid residues contained in the cationic polyamino acid segment may be appropriately set depending on the charge number desired for the segment. The cationic polyamino acid segment may include non-cationic amino acid residues as long as the effect of the present invention is not impaired. The number of non-cationic amino acid residues may be, for example, 20% or less, preferably 10% or less, more preferably 5% or less, even more preferably 2% or less, with respect to the total number of amino acid residues contained in the cationic polyamino acid segment.

The hydrophilic polymer chain segment may be formed of any appropriate hydrophilic polymer. Examples of the hydrophilic polymer include poly(ethylene glycol), polysaccharide, poly(vinylpyrrolidone), poly(vinyl alcohol), poly(acrylamide), poly(acrylic acid), poly(methacrylamide), poly(methacrylic acid), poly(methacrylic acid ester), poly(acrylic acid ester), polyamino acid, poly(malic acid), poly(oxazoline), and derivatives thereof. Specific examples of the polysaccharide include starch, dextran, fructan, and galactan etc. Of those, poly(ethylene glycol) may be preferably used because terminal-reactive polyethylene glycols having a variety of functional groups at their terminals are commercially available, and polyethylene glycols having a variety of molecular weights and branched polyethylene glycols are commercially available and are readily available.

The length of the hydrophilic polymer chain segment may be set to an appropriate length depending on the chain length of the nucleic acid contained in the unit structure. Specifically, the hydrophilic polymer chain segment is set so as to have a length that can cover the nucleic acid. In the present invention, when at least one hydrophilic polymer chain segment in the unit structure has a radius of inertia (Rg) equal to or longer than the length of the nucleic acid contained in the unit structure (when the unit structure includes a plurality of nucleic acids, the total length of the nucleic acids), it is adduced that the entirety of the nucleic acid is covered with the hydrophilic polymer chain segment(s). For example, because the radii of inertia (Rg) of poly(ethylene glycol) s having molecular weights of 21,000 Da and 42,000 Da are about 6.5 nm and about 9.7 nm, respectively, the poly(ethylene glycol) s are adduced to have the ability to cover siRNA (length: about 5.7 nm) by themselves. Further, in a unit structure including a hydrophilic polymer chain segment that is arranged so as to have a rotation center (for example, a linking site to a polyamino acid segment) on one terminus side of a nucleic acid and a hydrophilic polymer chain segment arranged so as to have a rotation center on the other terminus side of the nucleic acid, when the total of the radii of inertia (Rg) of the hydrophilic polymer chain segments on both termini of the nucleic acid is a length equal to or longer than that of the nucleic acid in the unit structure, it can be adduced that the entirety of the nucleic acid is covered with the hydrophilic polymer chain segments. In such a unit structure, each hydrophilic polymer chain segment preferably has a radius of inertia (Rg) equal to or longer than half the length of the nucleic acid, more preferably a radius of inertia (Rg) equal to or longer than the length of the nucleic acid, even more preferably a radius of inertia (Rg) 1.2 times or more longer than the length of the nucleic acid, still even more preferably a radius of inertia (Rg) 1.3 times or more longer than the length of the nucleic acid. This is because the entirety of the nucleic acid can be covered surely, and metabolism or decomposition of the nucleic acid is suitably avoided, resulting in improving the blood retentivity. However, in case the unit structure is formed of three or more block copolymers, each hydrophilic polymer chain segment arranged so as to have a rotation center on both terminus sides of the nucleic acid may have a radius of inertia (Rg) shorter than half the length of the nucleic acid as long as the entirety of the nucleic acid is enclosed by the comprehensive spatial extent derived from the hydrophilic polymer chain segment of each block copolymer. It should be noted that, with respect to the upper limit of the length of the hydrophilic polymer chain segment, the radius of inertia (Rg) thereof may be a length, for example, 2.5 times or less longer, preferably 1.6 times or less longer than the length of the nucleic acid contained in the unit structure. When the hydrophilic polymer chain segment has such a length, the unit structure is scarcely affected by steric hindrances or the like and can be advantageously formed. It should be noted that the radius of inertia (Rg) can be calculated based on the relationship between the molecular weight of the hydrophilic polymer constituting the hydrophilic polymer chain segment and the square of the radius of gyration. For example, in the case of poly(ethylene glycol), the radius of inertia (Rg) can be calculated by calculating a polymerization degree (DP) from the molecular weight and substituting the polymerization degree in the following equation (1) (Polymer 38, 2885-2891 (1997)).

$$Rg = 0.181 \times DP^{0.58} \tag{1}$$

In one preferred embodiment wherein the nucleic acid is siRNA, the unit structure is formed of one siRNA and two block copolymers, and the block copolymers each have double-stranded PEG at one terminal of the polyamino acid chain segment serving as the hydrophilic polymer chain segment. Each PEG chain has a molecular weight of preferably from 10,000 Da to 80,000 Da, more preferably from 20,000 Da to 60,000 Da, even more preferably from 30,000 Da to 45,000 Da.

In the block copolymer, the cationic polyamino acid segment and the hydrophilic polymer chain segment are linked to each other via any appropriate linking group. Examples of the linking group include an ester bond, an amide bond, an imino bond, a carbon-carbon bond, and an ether bond etc. Further, these segments may be linked to each other via a linking group that is cleavable in vivo (such as a disulfide bond, a hydrazone bond, a maleamate bond, or an acetal group). It should be noted that the cationic polyamino acid-side terminal and/or hydrophilic polymer chain-side terminal of the block copolymer may be subjected to any appropriate modification as long as the effect of the present invention is not adversely affected.

The target binding site may be any appropriate site depending on the target tissue, the purpose, or the like. The target binding site may be formed by binding a compound having the target binding site to the hydrophilic polymer chain-side terminal of the block copolymer. Any appropriate group may be used as the group for linking the target binding site to the hydrophilic polymer chain, and an example thereof is any appropriate amino acid residue. It should be noted that the term "target binding site" as used herein refers to a site capable of binding specifically to a substance derived from an organism or a virus to form a biological binding pair with the substance and having a biological recognition function.

As compounds having the target binding site, any appropriate compound may be bound depending on the target tissue, the purpose, or the like. Examples thereof include an antibody or a fragment thereof, or another protein having functionality or targeting properties, a peptide, an aptamer, a sugar such as lactose, and a physiologically active substance such as folic acid etc.

A preferred specific example of the block copolymer can be represented by the following general formula (1) or (2).

[Chem. 1]

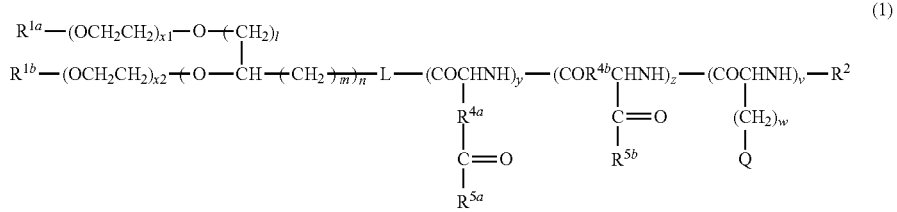

(1)

[Chem. 2]

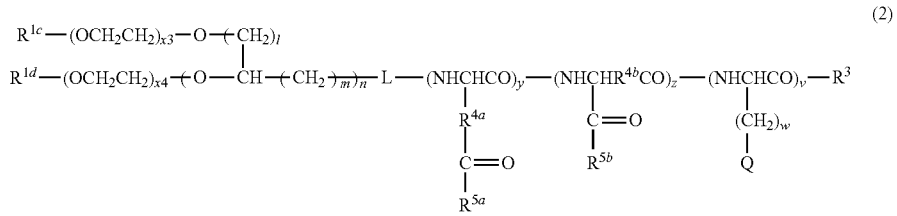

(2)

(In each of the formulae, $R^{1a}$ to $R^{1d}$ each independently represent a hydrogen atom, an unsubstituted or substituted linear or branched alkyl group having 1 to 12 carbon atoms, or a group represented by the following formula (I):

[Chem. 3]

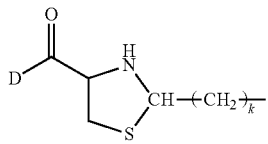

(I)

where k represents an integer of from 1 to 5, and D represent a target binding site;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

$R^{4a}$ and $R^{4b}$ each independently represent a methylene group or an ethylene group;

$R^{5a}$ and $R^{5b}$ are each independently selected from the same or different groups in the group consisting of the following groups:

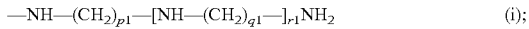  (i);

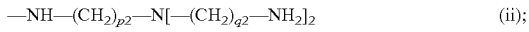  (ii);

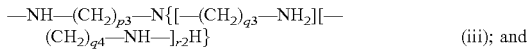  (iii); and

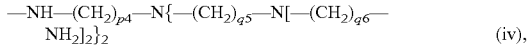  (iv), where p1 to p4, q1 to 6, and r1 and 2 are each independently an integer of from 1 to 5;

Q is $-NH_2$, $-NHC(=NH)NH_2$, or a group represented by the following formula (II);

[Chem. 4]

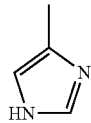

(II)

L is a divalent linking group or a valence bond;

x1 to x4 are each independently an integer of from 110 to 2,000;

y, z, and v are each independently an integer of from 0 to 60, provided that y, z, and v satisfy the relationship of $5 \leq y+z+v \leq 60$;

w is an integer of from 1 to 6;

l and m are each independently an integer of from 0 to 5; and n is 0 or 1.)

In formula (1) or (2), L is a divalent linking group or a valence bond. Any appropriate linking group can be utilized as the divalent linking group. For example, L can be $-L^1-L^2-L^3-$ in formula (1) and L can be $-L^4-L^5-L^6-$ in formula (2). In the formulae: $L^1$ and $L^4$ are each independently $-(O-(CH_2)_a)_b-L^{1a}$ where a is an integer of from 1 to 5 and b is an integer of from 0 to 300, and it is not necessary that all a's be identical to each other when b is 2 or more, and $L^{1a}$ is a valence bond, i.e., $-S-S-$, $-NH-$, $-O-$, $-O-CH(CH_3)-O-$, $-OCO-$, $-OCONH-$, $-NHCO-$, $-NHCOO-$, $-NHCONH-$, $-CONH-$, or COO; $L^2$ and $L^5$ are each independently a valence bond or $-L^{2a}-L^{2b}-L^{2c}-$, where $L^{2a}$ and $L^{2c}$ are structures acting as spacers, an example thereof is, but not particularly limited to, a substituted or unsubstituted alkyl group having 1 to 12 carbon atoms, and $L^{2b}$ is any one of structures represented by the following formulae (III) to (V); $L^3$ is $-(CH_2)_c-O)_d-(CH_2)_e-L^{3a}-$, where c is an integer of from 1 to 5, d is an integer of from 0 to 500, and e is an integer of from 0 to 5, and it is not necessary that all c's be identical to each other when d is 2 or more; $L^{3a}$ is $-NH-$ or $-O-$; and $L^6$ is $-((CH_2)_f-O)_g-(CH_2)_h-L^{6a}-(CH_2)_i-CO-$, where f is an integer of from 1 to 5, g is an integer of from 0 to 300, h is an integer of from 0 to 5, and i represent integers of from 0 to 5, and it is not necessary that all f's be identical to each other when g is 2 or more, and $L^{6a}$ is $-OCO-$, $-NHCO-$, $-OCONH-$, $-NHCOO-$, $-NHCONH-$, $-CONH-$, or $-COO-$.

[Chem. 5]

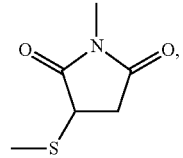

(III)

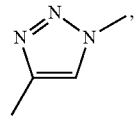

(IV)

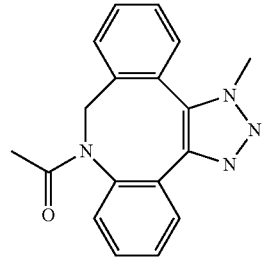

(V)

An alkyl moiety in the linear or branched alkyloxy group, alkyl-substituted imino group, and alkyl group having 1 to 12 carbon atoms, which are defined by the groups $R^{1a}$ to $R^{1d}$, $R^2$, and $R^3$ may be, for example, a methyl group, an ethyl group, a n-propyl group, an isopropyl group, a n-butyl group, a sec-butyl group, a tert-butyl group, a n-hexyl group, a decyl group, and an undecyl group etc. An alkenyl or alkynyl moiety in the linear or branched alkenyloxy group having 2 to 12 carbon atoms or the linear or branched alkynyloxy group having 2 to 12 carbon atoms may be exemplified by an alkenyl or alkynyl moiety including a double bond or a triple bond in the alkyl group having 2 or more carbon atoms as exemplified above.

For such group or moiety, a substituent in a "substituted" case may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkyl siloxy group, a siloxy group, or a silylamino group, or may be exemplified by an acetalized formyl group, a formyl group, or a halogen atom such as chlorine or fluorine. In this context, for example, the expression "$C_{1-6}$" means 1 to 6 carbon atoms and is used with the same meaning in the following description. In addition, an unsubstituted or substituted linear or branched alkyl moiety having 1 to 12 carbon atoms in the unsubstituted or substituted linear or branched alkylcarbonyl group having 1 to 24 carbon atoms may be selected with reference to the above mentioned examples, and an alkyl moiety having 13 or more carbon atoms may be, for example, a tridecyl group, a tetradecyl group, a pentadecyl group, a nonadecyl group, a docosanyl group, or a tetracosyl group.

The group selected from the group consisting of:

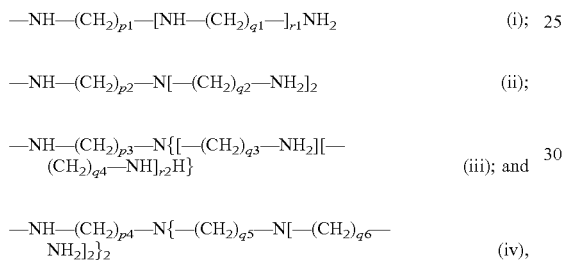

which is defined for the groups $R^{5a}$ and $R^{5b}$, is preferably the same group, more preferably a group of formula (i). In addition, p1 to p4 and q1 to 6 are each independently preferably 2 or 3, more preferably 2. Meanwhile, r1 and r2 are each independently preferably an integer of from 1 to 3. As groups $R^{5a}$ and $R^{5b}$, the same group may be selected for all repeating units including these groups, or different groups may be selected for the respective repeating units.

As Q, the same group may be selected for all repeating units including Q, or different groups may be selected for the respective repeating units. In addition, w is 1, 2, 3, or 4, for example.

x1 to x4, which represent the number of repeats of the ethylene glycol, are each a value that may be appropriately set depending on the length of the nucleic acid contained in the desired unit structure. For example, in case a unit structure including one double-stranded RNA having 21 base pairs is formed, x1 to x4 are each independently, as a lower limit, 120, 200, or 450, for example, and as an upper limit, 1,200, 1,000, or 850, for example.

y, z, and v are each a value that may be appropriately set depending on the negative charge number of the nucleic acid and the number of the block copolymer in the desired unit structure. For example, in case a unit structure including one double-stranded RNA having 21 base pairs and two block copolymers is formed, y, z, and v may be set so that the number of cationic groups in the cationic polyamino acid segment is an integer of preferably from 18 to 22, more preferably from 19 to 21, even more preferably 19 or 20. In this manner, the unit structure of the present invention is formed of two block copolymers, and the cationic polyamino acid segment in each of the block copolymers may include 18 to 22 cationic amino acid residues.

n is 0 or 1, preferably 1. According to a block copolymer having two poly(ethylene glycol) chains, it is possible to prepare a unit structure that significantly excels in blood retentivity.

D is preferably a peptide having 1 to 200 amino acid residues, more preferably a peptide having 1 to 100 amino acid residues, even more preferably a peptide having 1 to 30 amino acid residues.

Examples of the peptide include peptides capable of specifically binding to integrin, which is involved in angiogenesis, intimal thickening, and malignant tumor growth, and specific examples thereof include RGD peptides. By using an RGD peptide as the target binding site, particles, which are capable of specifically recognizing a diseased portion, and pharmaceutical compositions using the particles are obtainable. The RGD peptides as used herein refer to peptides that include an arginine-glycine-aspartic acid (RGD) sequence. The RGD peptide is preferably a cyclic RGD (cRGD) peptide. Specifically, D may represent a peptide represented by the following formula (VI).

[Chem. 6]

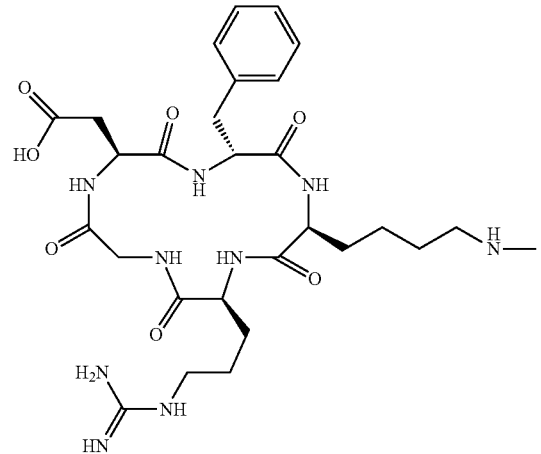

(VI)

In formula (1) or (2), the repeating units constituting the cationic polyamino acid segment are bound to each other in any suitable order, and it may be a random structure or a block structure.

The block copolymer can be prepared by any appropriate method. For example, an N-carboxylic anhydride (NCA) of a predetermined amino acid into which a protective group has been introduced as needed is sequentially polymerized using, as an initiator, a terminal amino group of a hydrophilic polymer (for example, poly(ethylene glycol)) aminated at the ω-terminal, and then deprotection or side chain exchange may be carried out to convert it into a polycation segment. Alternatively, a block copolymer having a polycation segment may be synthesized by first synthesizing a polyamino acid into which a protective group has been introduced as needed, and then binding the polyamino acid to a hydrophilic polymer, followed by deprotection or side chain exchange as needed. A variety of methods may be employed as the method of binding the polyamino acid to the hydrophilic polymer. These methods typically include a method involving introducing a reactive functional group at each terminal and performing coupling. Examples of these methods include: a method involving binding a carboxyl group to an amino group by using a condenser or by performing active esterification; a method involving using a maleimide and a thiol; and a method involving using an alkyne and an azide based on so-called click chemistry. Further, a block copolymer including a hydrophilic polymer having a target binding site at the terminal can be synthesized by: synthesizing a block copolymer using a hydrophilic polymer having a target binding site at the α-terminal or synthesizing a block copolymer using a hydrophilic polymer having a functional group capable of subsequently introducing a target binding site into the α-terminal; and then introducing the target binding site. A variety of methods may be employed as the introduction method for a target binding site. For example, the target binding site can be provided at the terminal on the hydrophilic polymer chain side by mixing in an acidic solution a block copolymer, in which the terminal on the hydrophilic polymer chain side has been acetalized, and a compound having a cysteine terminal and a desired target binding site.

<A-2. Nucleic Acid>

The nucleic acid means a poly- or oligonucleotide including, as basic units, nucleotides formed of a purine or pyrimidine base, a pentose, and phosphoric acid, and examples thereof may include oligo- or poly-double-stranded RNA, oligo- or poly-double-stranded DNA, oligo- or poly-single-stranded DNA, and oligo- or poly-single-stranded RNA. Further, oligo- or poly-double-stranded nucleic acid and oligo- or poly-single-stranded nucleic acid in each of which RNA and DNA exist in a mixed state in the same chain are also included. The nucleotide contained in the nucleic acid may be of a natural type or of a chemically modified non-natural type, or may have added thereto an amino group, a thiol group, a fluorescent compound, or any other molecule.

The chain length of the nucleic acid may be, for example, from 4 to 20,000 bases, preferably from 10 to 10,000 bases, more preferably from 18 to 30 bases.

In consideration of its functions or actions, examples of the nucleic acid may include plasmid DNA, siRNA, micro RNA, shRNA, an antisense nucleic acid, a decoy nucleic acid, an aptamer, and a ribozyme.

As the siRNA, for example, there may be used all those designed for a target gene or a polynucleotide by any appropriate method. Regarding the chain length of the siRNA, the part constituting the double strand may have a length of preferably from 15 to 50 bases, more preferably from 18 to 30 bases; compounds known in the art and all nucleotides having effects or functions similar to those of the compounds are encompassed. Specific examples of the siRNA include, but are not limited to, ones that may be designed with reference to a gene to be targeted by gene therapy.

<A-3. Preparation Method for Unit Structures>

The unit structures of the present invention can be prepared, for example, by mixing the block copolymer(s) and the nucleic acid such as siRNA in an aqueous solution that is buffered as needed (for example, phosphate buffered saline, HEPES buffer).

<B. Pharmaceutical Preparations>

The pharmaceutical preparations of the present invention include the unit structure described in section A. In one embodiment, the pharmaceutical preparation of the present invention can be obtained by mixing the block copolymer(s) and the nucleic acid in an aqueous solution that is buffered as needed so as to achieve an N/P ratio of preferably from 1.0 to 2.5, more preferably from 1.1 to 2.0, even more preferably from 1.2 to 1.6. When the N/P ratio is adjusted to this range, free nucleic acids or block copolymers may be reduced to obtain a pharmaceutical preparation having the unit structures at a high content. In addition, when the N/P ratio is adjusted to the range of from 1.1 to 2.0 or from 1.2 to 1.6, a pharmaceutical preparation including a higher content of the unit structure and a certain amount of a block copolymer free of electrostatic bonds with the nucleic acid (free block copolymer) can more significantly achieve both the improvement in blood retentivity and the anti-tumor effect of the nucleic acid because it is possible to balance to a higher order the re-capturing action of the free nucleic acid by the free block copolymer(s) with the smooth release of the nucleic acid from the unit structure into the target cell. Herein, the N/P ratio means [total number (N) of cationic groups in block copolymer]/[total number (P) of phosphate groups in nucleic acid].

In another embodiment, the pharmaceutical preparation of the present invention can be obtained by mixing the block copolymer(s) and the nucleic acid in an aqueous solution that is buffered as needed so as to achieve an N/P ratio of more than 2.5, for example, an N/P ratio of preferably 3 or more, more preferably 5 or more, even more preferably 10 or more. As mentioned above, when the N/P ratio is raised, the stability in blood of the nucleic acid contained in the pharmaceutical preparation can be improved significantly. The upper limit of the N/P ratio is, for example, 50, 30, or 20.

EXAMPLES

Hereinafter, although the present invention is more specifically described by way of Examples, the present invention is not limited to Examples below. It should be noted that in the Examples below, the polymer structures are identified in the order of the molecular weight (kDa) of PEG and the polymerization degree of a polyamino acid. In addition, when the block copolymer includes a plurality of PEG chains, the polymer structure is identified in the order of the molecular weight (kDa) of PEG, the number of the chains, and the polymerization degree of the polyamino acid. For example, when the hydrophilic polymer chain segment is formed of a 2-arm Branched PEG, each arm of which has a molecular weight of 10 kDa, and the cationic polyamino acid segment is formed of 20 lysine residues, the polymer is abbreviated as "PEG-PLys (10×2-20)".

<Preparation of Block Copolymers>

0.80 g of a 2-arm Branched poly(ethylene glycol) derivative (manufactured by NOF CORPORATION, product name "SUNBRIGHT GL2-400PA", average molecular weight=42,000 Da (21,000 Da×2)), which is illustrated by the following formula (3) and was purified with an ion-exchange column (manufactured by GE Healthcare Japan, product name "CM-Sephadex C-50"), and 1.07 g of thiourea were weighed in a recovery flask, and the mixture was subjected to argon substitution, followed by addition of 12 ml of N,N-dimethylformamide (DMF). The mixture was heated to dissolve the components and stirred for an additional 2 hours. 0.13 g (corresponding to 25 equivalents) of Nε-trifluoroacetyl-L-lysine N-carboxylic anhydride (Lys (TFA)-NCA) was weighed in a recovery flask under argon and was dissolved in 2 ml of DMF. Using a syringe, the resultant solution was added to the recovery flask containing the 2-arm Branched PEG. The mixture was allowed to react with stirring under argon in a water bath at 25° C. for 2 days. Disappearance of an absorption peak specific to NCA was confirmed by IR, and 7 ml of methanol were added thereto. The resultant solution was poured into 210 ml of cold diethyl ether with stirring to perform precipitation. The procedure, which included removing the supernatant, adding 14 ml of methanol, heating the mixture to dissolve the precipitates, and then pouring in cold diethyl ether to perform precipitation, was further repeated twice. The precipitates were filtered using a filter and dried under vacuum to afford 0.85 g of PEG-PLys (TFA) as a white powder. 0.40 g of the PEG-PLys (TFA) was dissolved in 40 ml of methanol. 4 ml of an aqueous solution of 1 N NaOH were added to the resultant solution, and the mixture was allowed to react with stirring in a water bath at 35° C. for 17 hours. The reaction solution was put into a dialysis tube (MWCO=6,000 to 8,000) and was dialyzed four times against 0.01 N hydrochloric acid used as an external solution and three times against pure water used as an external solution. The liquid in the tube was lyophilized to afford 0.35 g of PEG-PLys (hydrochloride) as a white powder. The polymerization degree of PLys was determined to be 20 by $^1$H-NMR. In addition, GPC revealed that a block copolymer: PEG-PLys (21×2-20) was obtained.

[Chem. 7]

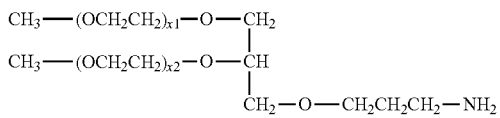

(3)

(In the formula, x1 and x2 are each from about 450 to 470.)

In the same manner as above, a variety of block copolymers including different kinds of PEGs and/or having different polymerization degrees of polylysine were obtained.

<Preparation of Pharmaceutical Preparations>

The block copolymers and siRNAs were separately dissolved in 10 mM HEPES buffer (pH 7.3), and the resultant solutions were mixed so as to achieve predetermined N/P ratios to prepare pharmaceutical preparations. The sequences of the siRNAs used are shown below (the lower-case letters represent modification sites by 2'-O-methylation). It should be noted that the siRNAs were labeled with a fluorescent molecule such as Cy5 as needed before use. In addition, the 5'-terminals of the siRNAs were dephosphorylated.

(1) siGL3 (siRNA against firefly luciferase):

Sense strand:
(SEQ ID NO: 1)
5'-CUUACGCUGAGUACUUCGAdTdT-3'

Antisense strand:
(SEQ ID NO: 2)
5'-UCGAAGUACUCAGCGUAAGdTdT-3'

(2) sihVEGF (siRNA against human vascular endothelial growth factor):

Sense strand:
(SEQ ID NO: 3)
5'-GAUCUCAUCAGGGUACUCCdTdT-3'

Antisense strand:
(SEQ ID NO: 4)
5'-GGAGUACCCUGAUGAGAUCdTdT-3'

(3) siPLK1 (siRNA against polo-like kinase 1):

Sense strand:
(SEQ ID NO: 5)
5'-AGAuCACCCuCCUuAAAuAUU-3'

Antisense strand:
(SEQ ID NO: 6)
5'-UAUUUAAgGAGGGUGAuCUUU-3'

<Structural Determination of the Unit Structures>

Table 1 shows the compositions of the unit structures in the pharmaceutical preparations (N/P=1) prepared using a variety of block copolymers and Cy5-siGL3. The conditions for measurement are as described below.

(1) Polymerization Degree of Polylysine

Nuclear magnetic resonance spectra ($^1$H-NMR spectra) were measured with a nuclear magnetic resonance apparatus (manufactured by JEOL Ltd., product name "JNM-ECS400") using D2O as the solvent at a temperature of 25° C. The polymerization degree of polylysine was determined by calculating the number of methylene groups in the side chains of the polylysine based on the $^1$H-NMR spectrum.

(2) Molecular Weights of the Unit Structures

The molecular weights of the unit structures were measured with an ultracentrifuge for analysis (manufactured by Beckman Coulter, product name "Optima XL-A") in 10 mM HEPES buffer containing 150 mM NaCl at 20° C.

(3) Number of siRNAs in the Unit Structures

The number of fluorescent molecules derived from Cy5-siRNA was determined by fluorescence correlation spectroscopy with a confocal laser scanning microscope (manufactured by Carl Zeiss, product name "LSM510") equipped with a 40× objective lens (C-Apochromat, manufactured by Carl Zeiss) and a ConfoCor3 module in 10 mM HEPES buffer containing 150 mM NaCl at room temperature. The number of siRNAs in the unit structures was estimated based upon the number of fluorescent molecules derived from only siRNA.

(4) Number of Block Copolymers in the Unit Structures

The number of block copolymer(s) was calculated from the molecular weight of PEG and the values of items (1) to (3).

TABLE 1

|  | Block copolymer | Molecular weight of PEG (Da) | Polymerization degree of polylysine | Molecular weight of unit structure (Da) | Number of siRNAs in unit structure | Number of block copolymers in unit structure | Sum of charges | Covering with PEG*[1] |
|---|---|---|---|---|---|---|---|---|
| Example | PEG-PLys (12-21) | 12,000 | 21 | 42,400 | About 1 | About 2 | +2 | ○ |
|  | PEG-PLys (21-21) | 21,000 | 21 | 56,800 | About 1 | About 2 | +2 | ○ |

TABLE 1-continued

|  | Block copolymer | Molecular weight of PEG (Da) | Polymerization degree of polylysine | Molecular weight of unit structure (Da) | Number of siRNAs in unit structure | Number of block copolymers in unit structure | Sum of charges | Covering with PEG[*1] |
|---|---|---|---|---|---|---|---|---|
|  | PEG-PLys (42-18) | 42,000 | 18 | 95,000 | About 1 | About 2 | −4 | ○ |
|  | PEG-PLys (10 × 2-22) | 10,000 × 2 | 22 | 52,700 | About 1 | About 2 | +4 | ○ |
|  | PEG-PLys (21 × 2-20) | 21,000 × 2 | 20 | 99,100 | About 1 | About 2 | 0 | ○ |
|  | PEG-PLys (37 × 2-19) | 37,000 × 2 | 19 | 149,900 | About 1 | About 2 | −2 | ○ |
| Comparative Example | PEG-PLys (21-88) | 21,000 | 88 | 61,800 | About 2 | About 1 | +8 | x |
|  | PEG-PLys (21 × 2-89) | 21,000 × 2 | 89 | 82,400 | About 2 | About 1 | +9 | x |

[*1]When at least one PEG chain in the unit structure has a radius of inertia (Rg) equal to or greater than the length of the siRNA contained in the unit structure (when the unit structure contains a plurality of siRNAs, the total of the lengths of the siRNAs), the unit structure is evaluated as Symbol "○" because the entirety of the siRNA is covered with the PEG chain, or as Symbol "x" otherwise. However, in the unit structured formed of one siRNA and two block copolymers, the PEG chain is considered to be arranged so that each of the two termini of the siRNA is a rotation center. When the total of the radii of inertia (Rg) of the PEG chains of the respective termini is equal to or greater than the length of the siRNA, it is judged that the entirety of the siRNA is covered with the PEG chains.

<Blood Retentivity of siRNA>

Figure 2A:
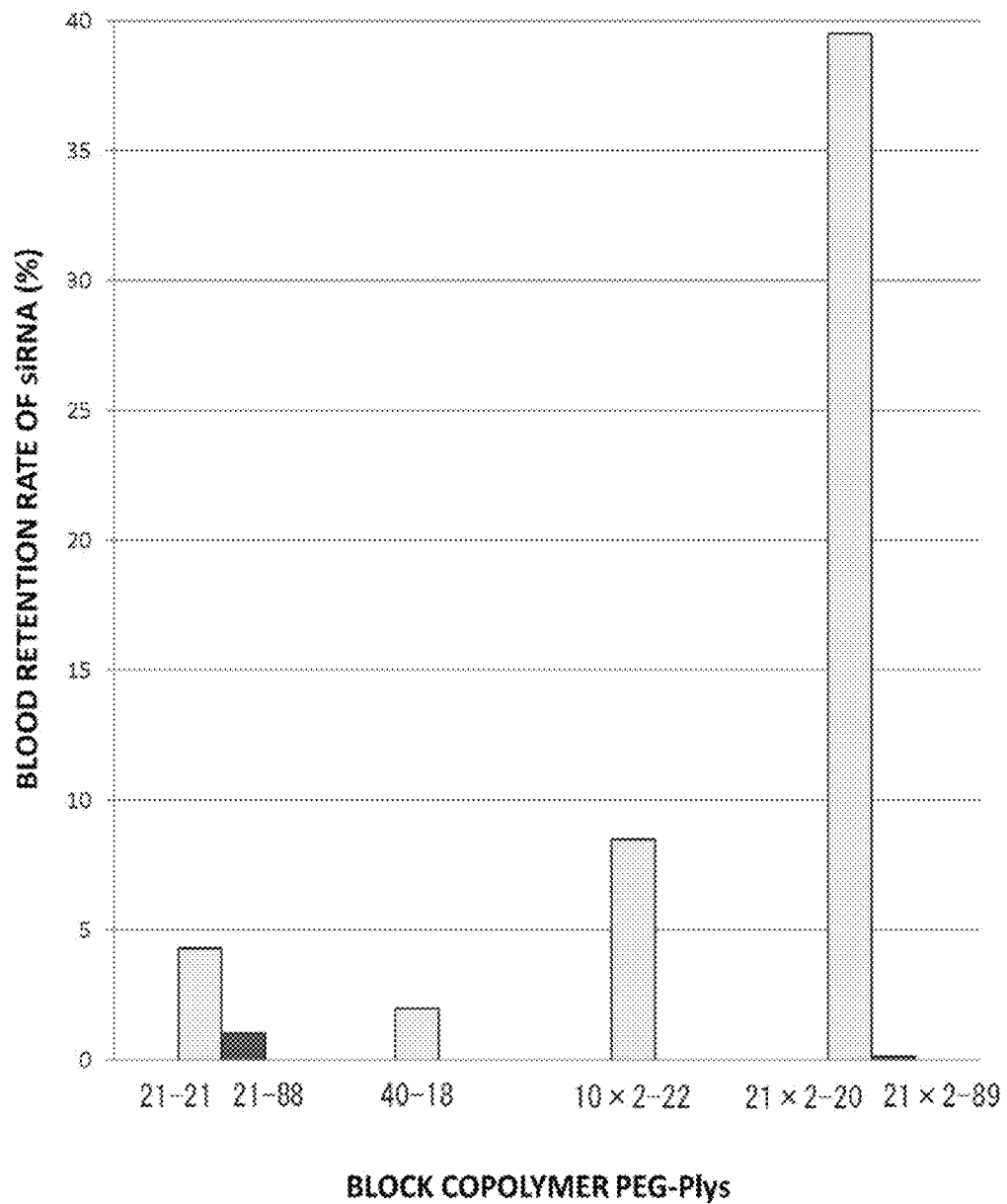
FIG. 2A is a graph showing blood retention rates of siRNAs 10 minutes after administration of unit structures.
Figure 2B:
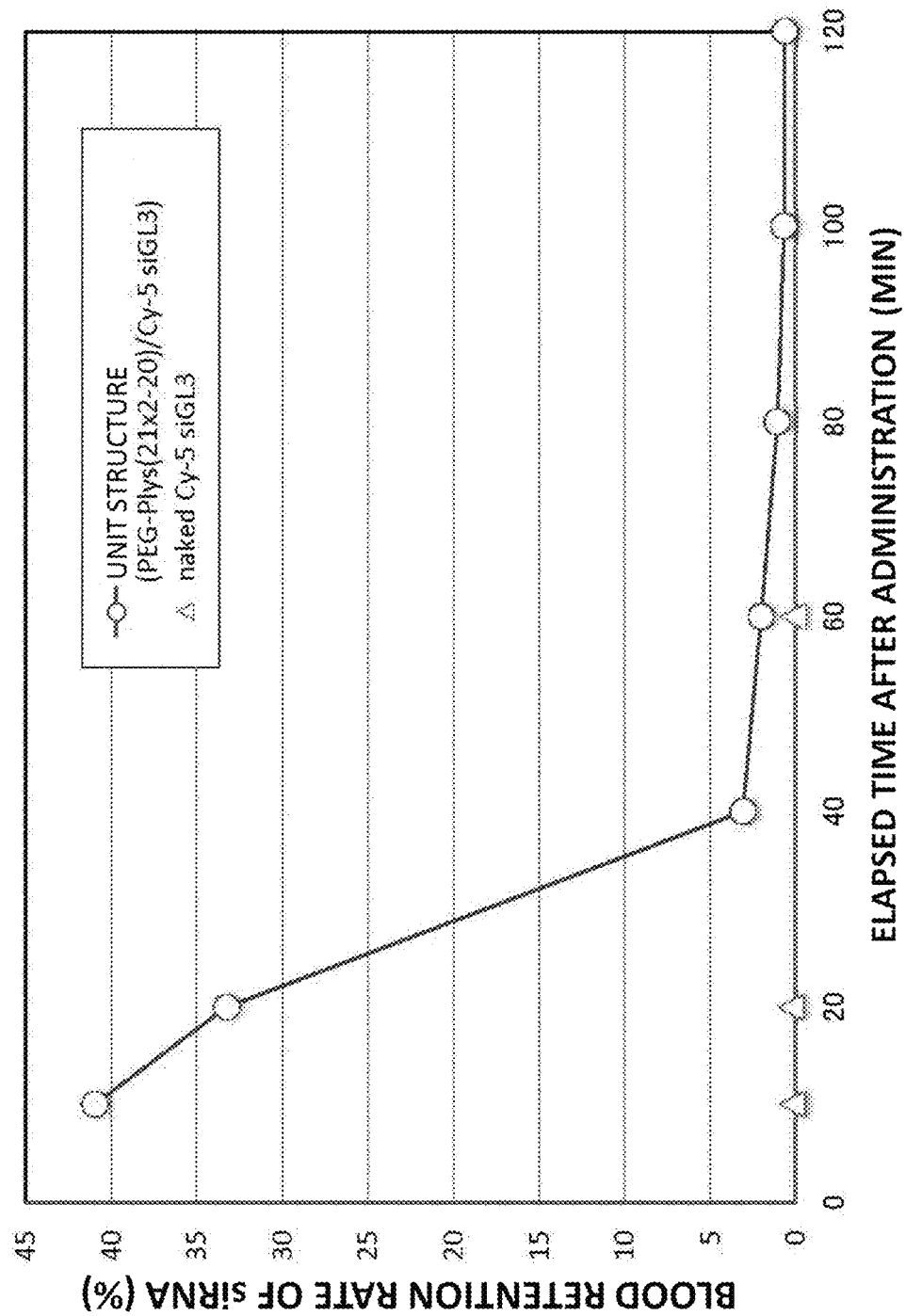
FIG. 2B is a graph showing changes in blood retention rates of siRNAs up to 120 minutes after administration of unit structures.

The pharmaceutical preparations (N/P=1.4) prepared using different block copolymers or naked siRNA were respectively administered to the tail veins of 6-week-old male BALB/c-nu mice. At this time, the administration was carried out so that the dose was 24 μg of the siRNA. In addition, Cy5-siGL3 was used as the siRNA that forms the unit structure. After that, blood samples were collected with heparin from the mice over time, and the amount of Cy5 in the serum was determined by using a micro-volume spectrophotometer (manufactured by Thermo Fisher Scientific, product name "NanoDrop"). Subsequently, the blood retention rate of siRNA was determined by the following equation. FIG. 2A shows the blood retention rates of siRNA (N=3) 10 minutes after the administration of each pharmaceutical preparation. Further, FIG. 2B shows the change in blood retention rates of the siRNA (N=1) up to 120 minutes after the administration of the pharmaceutical preparation.

Blood retention rate (%) of siRNA={(Amount of Cy5 in serum)/(Total amount of Cy5 administered)}×100

As shown in FIG. 2A, the pharmaceutical preparations of the present invention exceled in blood retentivity of siRNA 10 minutes after the administration as compared to the pharmaceutical preparations of the Comparative Examples. In particular, the unit structure including the block copolymer having two PEG chains achieved siRNA blood retention rates that significantly exceled. In addition, as shown in FIG. 2B, although the blood retention rate 10 minutes after the administration was almost 0% when the naked siRNA was administered, the blood retention rate of the siRNA 10 minutes after the administration was 40% or more when the pharmaceutical preparation of the present invention was administered, and the siRNA even remained in the blood 60 minutes after the administration.

<Accumulation of Unit Structures in Target Cells>

Figure 3:
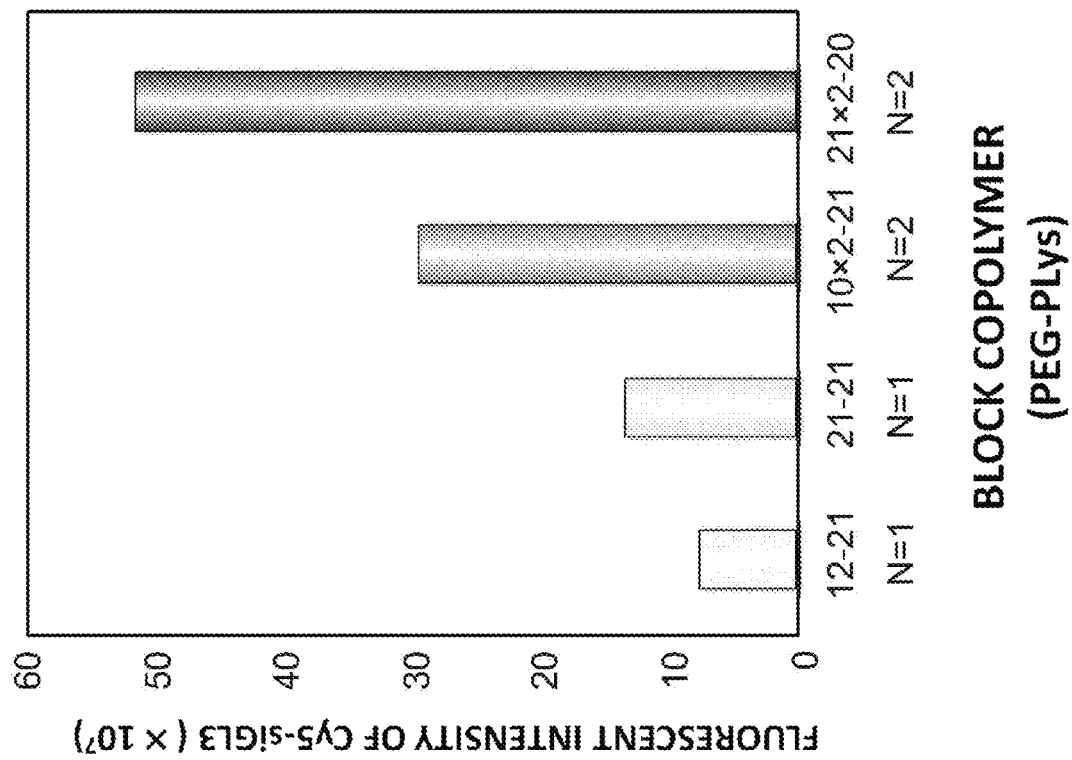
FIG. 3 is a graph showing fluorescent intensities of Cy5 in cancer tissues 4 hours after administration of unit structures.

Kidney cancer cells (OS-RC-2) were implanted subcutaneously in 6-week-old male BALB/c-nu mice at 1×10$^7$ cells/200 μl. On day 6 after the implantation of the cancer cells, pharmaceutical preparations (N/P=1.4) prepared using different block copolymers were respectively administered to the tail veins of the mice. At this time, the administration was carried out so that the dose was 24 μg of the siRNA. In addition, Cy5-siGL3 was used as the siRNA that forms the unit structure. 4 hours after the administration, the subcutaneously-implanted cancer tissues were removed, and the fluorescent intensities of Cy5 were measured by IVIS. FIG. 3 shows the results.

As shown in FIG. 3, in the subcutaneous cancer tissues of the mice to which the pharmaceutical preparations of the present invention were administered, strong fluorescent signals attributed to Cy5-siGL3 were detected. From this, it can be deduced that the unit structures administered to the tail veins were efficiently taken up into the cancer cells from the blood.

<In Vitro RNAi Activity of the Unit Structures>

Figure 4:
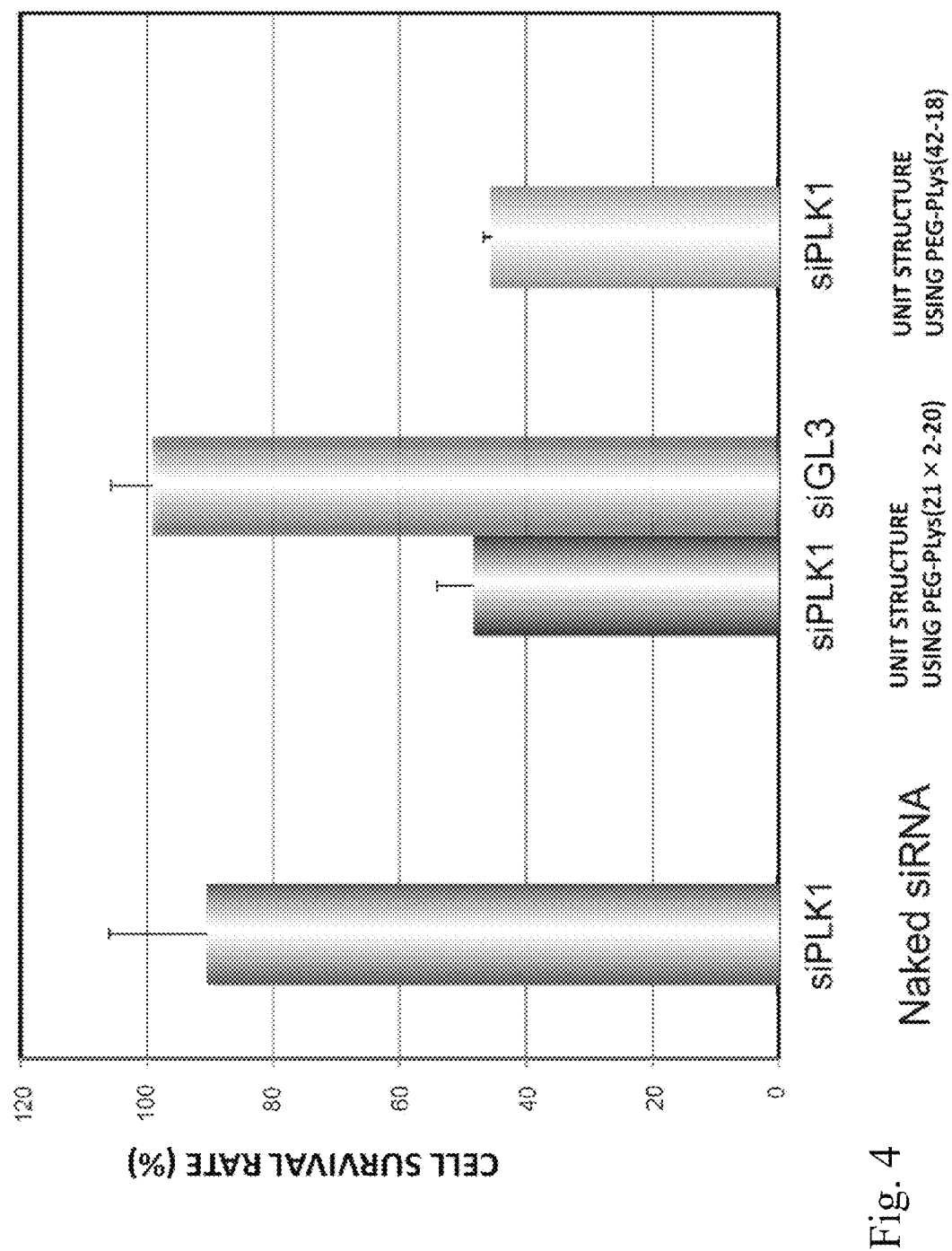
FIG. 4 is a graph showing in vitro RNAi activities of unit structures.

Kidney cancer cells (OS-RC-2) were seeded into a 12-well culture dish so as to achieve 80% confluency, and cultured in RPMI medium containing 10% FCS, penicillin (100 U/ml), and streptomycin (100 μg/ml) for 48 hours. Subsequently, the medium was exchanged, and each of pharmaceutical preparations (N/P=1.4) prepared using different block copolymers or naked siRNA was added thereto. At this time, the addition was carried out so that the concentration of siRNA was 900 nM/well. In addition, siPLK1 or siGL3 (control) was used as the siRNA that forms the unit structures. The cells were cultured for 48 hours, and the number of surviving cells was measured with "Cell Counting Kit 8" (product name, manufactured by DOJINDO LABORATORIES), and the cell survival rate was calculated (N=4). FIG. 4 shows the results.

As shown in FIG. 4, the survival rate of the cells cultured together with the pharmaceutical preparation containing siGL3 or naked siPLK1 was 90% or more, while both of the survival rates of the cells cultured together with the pharmaceutical preparations containing siPLK1 were less than 50%. This suggests that the unit structures of the present invention can deliver siRNA into cells more suitably than the naked siRNA and can suppress expression of the PLK1 gene in a sequence-specific manner.

<Anti-Tumor Effect of Unit Structure 1>

Figure 5:
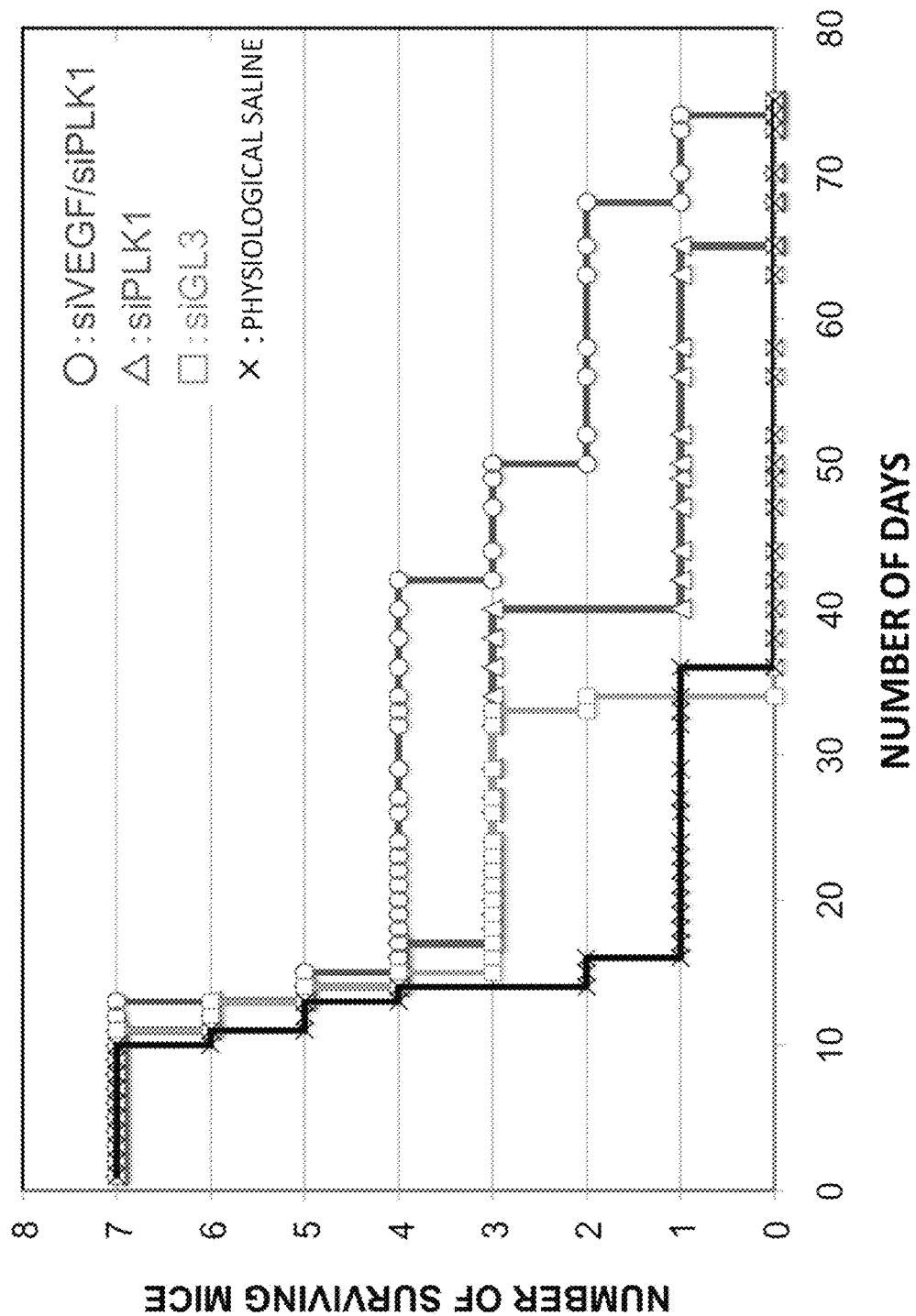
FIG. 5 is a graph showing the relationship between the number of days elapsed after the start of administration of samples and the number of surviving mice.

Kidney cancer cells (OS-RC-2) were implanted subcutaneously in 6-week-old male BALB/c-nu mice at 1×10$^7$ cells/200 μl. From day 6 after the implantation of the cancer cells, pharmaceutical preparations (N/P=1.4) prepared using different siRNAs so that the dose was 24 μg of the siRNAs, or physiological saline, were respectively administered to the tail veins of the mice once every 3 days up to day 39. At this time, PEG-PLys(21×2-20) was used as the block copolymer that forms the unit structure. In addition, for the group to which both of sihVEGF and siPLK1 were administered, the siRNAs were used in equal amounts (molar basis). FIG. 5 shows the relationship between the number of days elapsed after the start of the administration and the number of surviving mice (N=7).

As shown in FIG. 5, it was found that the mice, to which only siPLK1 or both of sihVEGF and siPLK1 as the siRNA were administered, survived longer than the mice to which physiological saline or siGL3 as the siRNA was administered.

<Anti-Tumor Effect of Unit Structure 2>

Figure 6A:
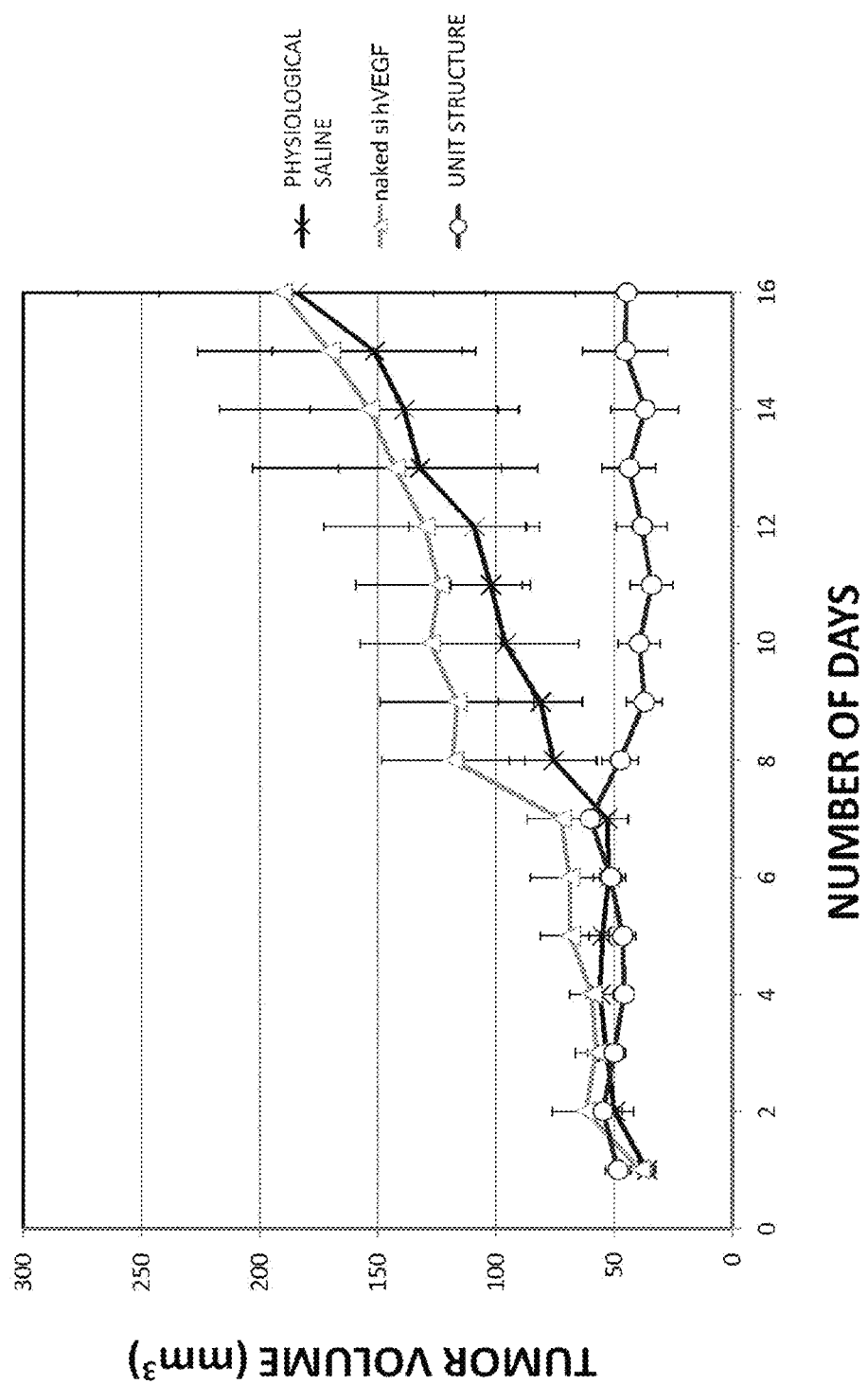
FIG. 6A is a graph showing changes in tumor volume after the start of administration of samples.
Figure 6B:
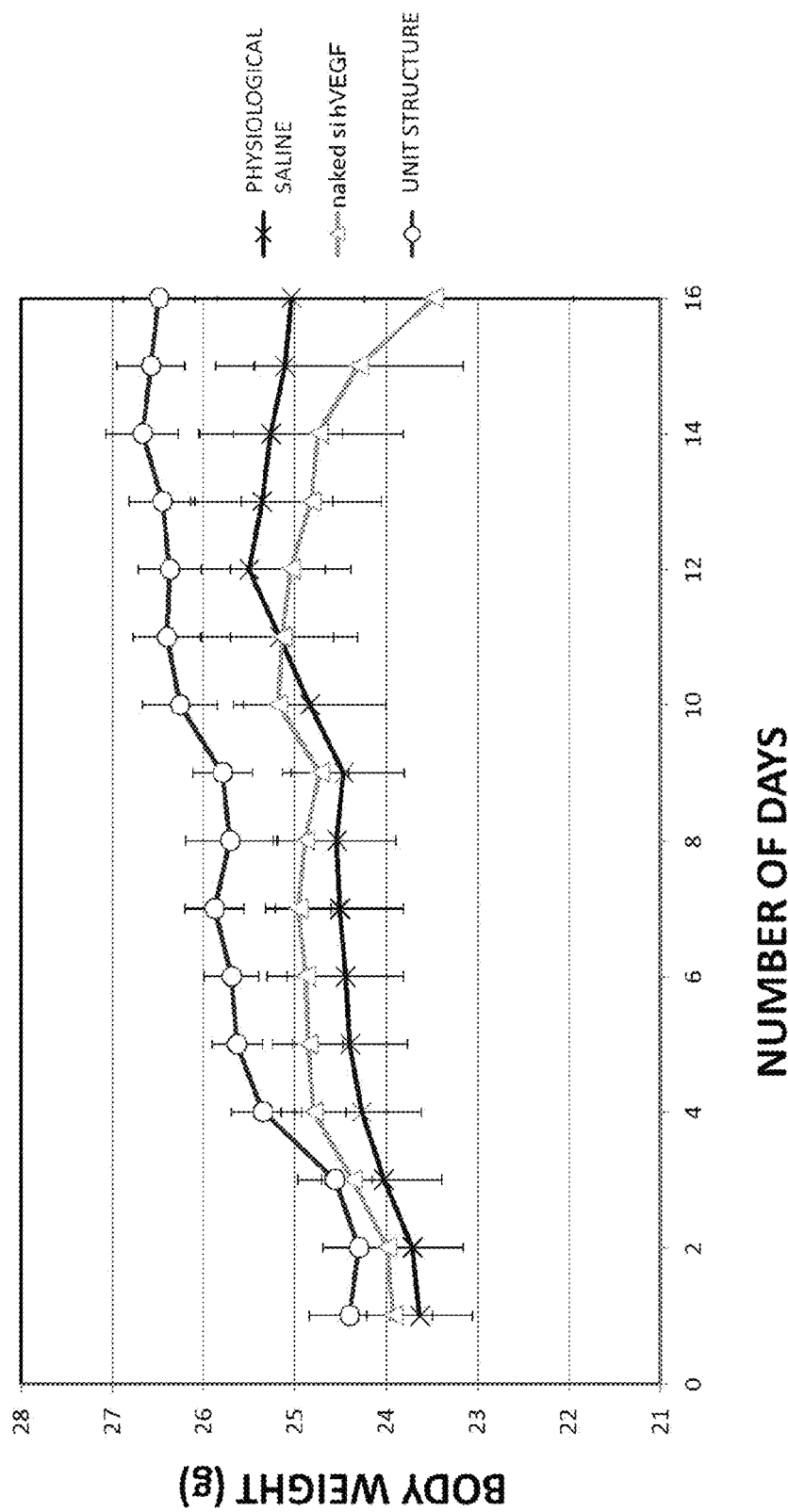
FIG. 6B is a graph showing changes in body weight after the start of administration of the samples.

Kidney cancer cells (OS-RC-2) were implanted subcutaneously in 9-week-old male BALB/c-nu mice at $1\times10^7$ cells/200 µl. The day when a cancer tumor mass was observed for the first time was defined as treatment day 1, and the pharmaceutical preparation (N/P=1.4), naked siRNA, or physiological saline was administered to the tail veins of the mice once a day for 20 days so that the dose was 24 µg of the siRNA. At this time, sihVEGF was used as the siRNA that forms the unit structure, and PEG-PLys(21×2-20) was used as the block copolymer. FIGS. 6A and 6B respectively show the changes in tumor volume and the changes in body weight after the start of the administration (N=8 to 10).

As shown in FIG. 6A, in the mice to which physiological saline or naked siRNA was administered, the tumor volume increased as the days passed; on the other hand, in the mice to which the pharmaceutical preparation of the present invention was administered, the tumor volume was suppressed to a constant level or was reduced, and a significant anti-tumor effect was confirmed. In addition, as shown in FIG. 6B, in the mice to which the unit structure of the present invention was administered, a reduction of the body weight was not seen.

Further, tumors were removed from the mice on treatment day 21, and RNAs were extracted using an RNA extraction reagent (manufactured by NIPPON GENE CO., LTD., product name "Isogen") according to the method described in the manual. The amounts of the resultant RNAs were determined with a micro-volume spectrophotometer (manufactured by Thermo Fisher Scientific, product name "NanoDrop"). cDNAs were synthesized from the samples, and the hVEGF mRNA expression levels were determined by RT-PCR. The expression levels (averages) in the group to which physiological saline was administered, the group to which naked siRNA was administered, and the group to which the pharmaceutical preparation was administered were found to be 0.415 (N=6), 0.364 (N=3), and 0.191 (N=2), respectively, as values relative to a housekeeping gene. These results reveal that sihVEGF exhibited a high RNAi effect in the group to which the pharmaceutical preparation was administered and support the above mentioned anti-tumor effect.

<Anti-Tumor Effect of Unit Structure 3>

Figure 7A:
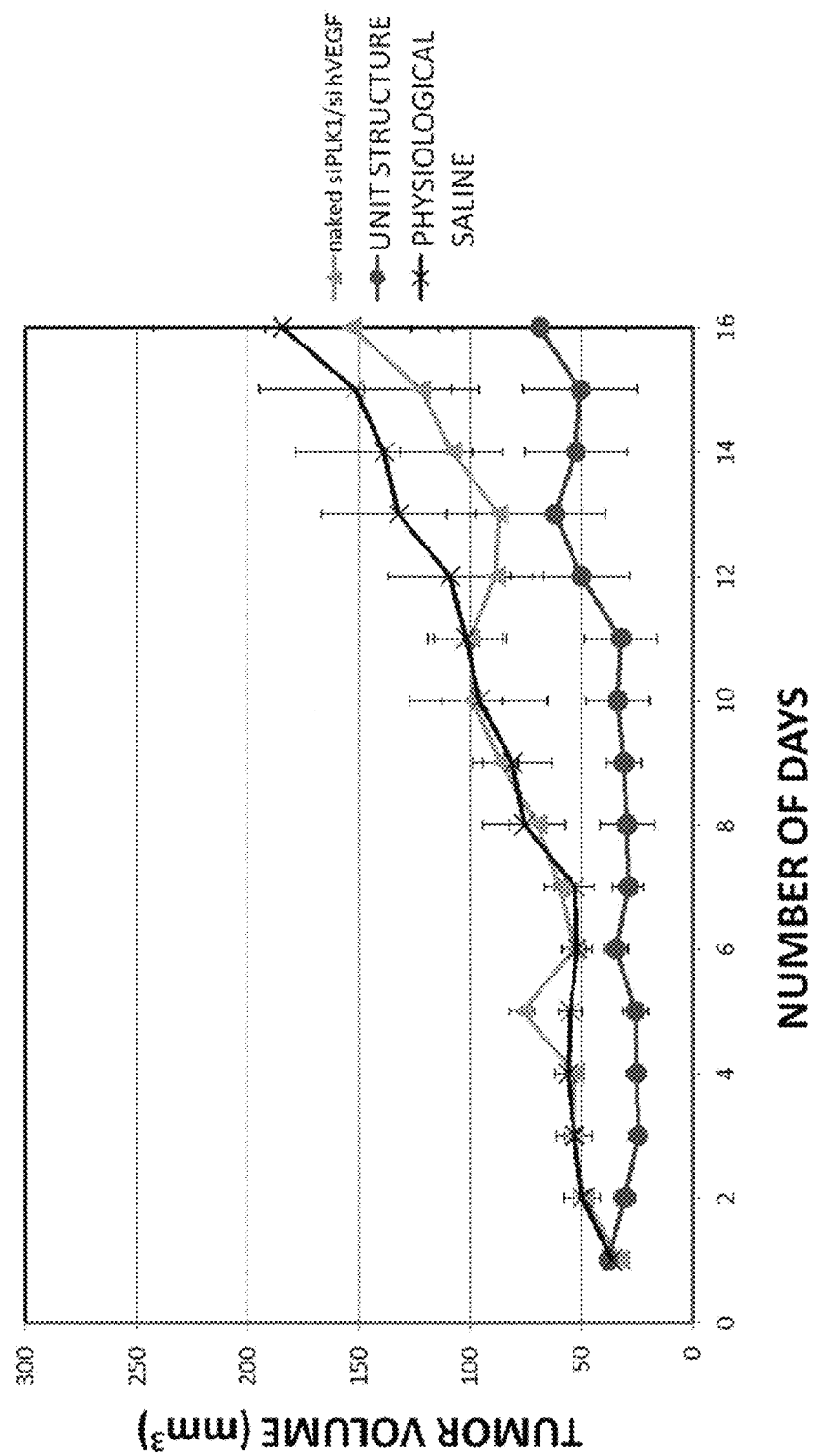
FIG. 7A is a graph showing changes in tumor volume after the start of administration of samples.
Figure 7B:
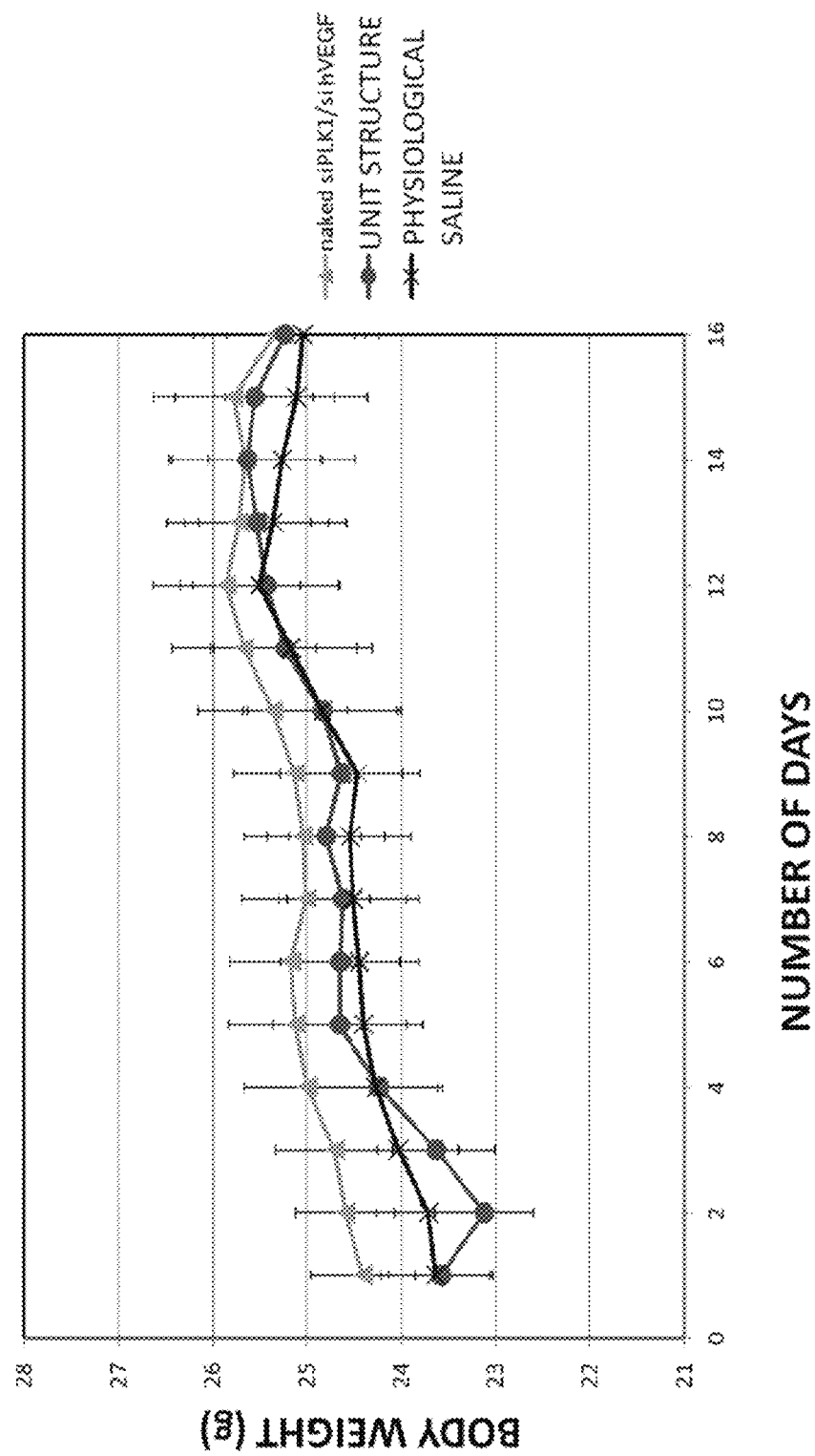
FIG. 7B is a graph showing changes in body weight after the start of administration of the samples.

Kidney cancer cells (OS-RC-2) were implanted subcutaneously in 9-week-old male BALB/c-nu mice at $1\times10^7$ cells/200 µl. The day when a cancer tumor mass was observed for the first time was defined as treatment day 1, and the pharmaceutical preparation (N/P=2.5), naked siRNA, or physiological saline was administered to the tail veins of the mice once a day for 20 days so that the dose was 24 µg of the siRNA. At this time, sihVEGF and siPLK1 were used in equal amounts (molar basis) as the siRNA that forms the unit structure, and PEG-PLys (21×2-20) was used as the block copolymer. FIGS. 7A and 7B respectively show the changes in tumor volume and the changes in body weight after the start of the administration (N=8 to 10).

As shown in FIG. 7A, in the mice to which the pharmaceutical preparation of the present invention was administered, an increase in tumor volume was significantly suppressed as compared to the mice to which physiological saline or naked siRNA was administered, and the pharmaceutical preparation of the present invention was found to have a significant anti-tumor effect. In addition, as shown in FIG. 7B, there were no significant differences among the body weights of the mice.

Further, tumors were removed from the mice on treatment day 21, and extraction of RNAs and synthesis of cDNAs were carried out in the same manner as in the <Anti-tumor effect of unit structure 2> section. According to the results of RT-PCR using the obtained cDNAs, the expression levels (averages) of hVEGF mRNA in the group to which physiological saline was administered, the group to which naked siRNA was administered, and the group to which the pharmaceutical preparation was administered were found to be 0.415 (N=6), 0.520 (N=6), and 0.254 (N=4), respectively, as values relative to a housekeeping gene. In addition, the expression levels (averages) of PLK1 mRNA were found to be 0.0065 (N=5), 0.0064 (N=8), and 0.0041 (N=6), respectively, as values relative to a housekeeping gene. These results reveal that sihVEGF and siPLK1 exhibited high RNAi effects in the group to which the pharmaceutical preparation was administered and support the above mentioned anti-tumor effect.

<Blood Retentivity of siRNA when the Chain Length of Hydrophilic Polymer Chain Segment is Changed>

The pharmaceutical preparations (N/P=10) shown in Table 2 were administered to the tail veins of 6-week-old male BALB/c-nu mice. At this time, the administration was carried out so that the dose was 24 µg of the siRNA. In addition, Alexa647-siGL3 was used as the siRNA. After that, blood samples were collected with heparin from the mice over time, and the amounts of Alexa647 in the serum were determined with a micro-volume spectrophotometer (manufactured by Thermo Fisher Scientific, product name "NanoDrop").

TABLE 2

| | | Molecular weight of PEG (Da) | Polymerization degree of polylysine | Unit structure | | |
|---|---|---|---|---|---|---|
| Pharmaceutical preparation | Block copolymer | | | Number of siRNAs | Number of block copolymers | Sum of charges |
| A | PEG-PLys (21 × 2-20) | 21,000 × 2 | 20 | About 1 | About 2 | 0 |
| B | PEG-PLys (37 × 2-19) | 37,000 × 2 | 19 | About 1 | About 2 | −2 |

As a result, in the pharmaceutical preparation A obtained using a block copolymer having a 2-arm Branched PEG, each arm of which had a molecular weight of 21 kDa, the half-life of the fluorescent intensity attributed to Alexa647 was 57 minutes. On the other hand, in the pharmaceutical preparation B obtained using a block copolymer having a 2-arm Branched PEG, each arm of which had a molecular weight of 37 kDa, the half-life of the fluorescent intensity attributed to Alexa647 was 160 minutes. This revealed that a long blood retentivity of siRNA of about 1 hour was able to be achieved by using 2-arm Branched PEGS as the hydrophilic polymer chain. Further, the results show that, when the chain length of PEG is increased, the blood retentivity of siRNA can be significantly improved.

<Blood Retentivity of siRNA when the N/P Ratio is Changed>

Pharmaceutical preparations prepared so as to have a variety of N/P ratios were administered to the tail veins of 6-week-old male BALB/c-nu mice. At this time, the administration was carried out so that the dose was 24 μg of the siRNA. Alexa647-siGL3 was used as the siRNA, and PEG-PLys(37×2-19) was used as the block copolymer. The blood retentivity was calculated by measuring the fluorescent intensities of Alexa647-siGL3 flowing in the bloodstream of the auricular dermis deep layers of the mice with an in vivo confocal fluorescence microscope (manufactured by Nikon Corporation, product name "A1R").

As a result, the half-life of the fluorescent intensity attributed to Alexa647 was about 10 minutes when the N/P ratio was 1, about 55 minutes when the N/P ratio was 3, about 75 minutes when the N/P ratio was 5, and about 160 minutes when the N/P ratio was 10. This reveals that when the N/P ratio is increased, the blood retentivity of siRNA can be significantly improved.

INDUSTRIAL APPLICABILITY

The unit structure of the present invention can be suitably applied in a drug delivery system for a nucleic acid pharmaceutical or the like.

EXPLANATION OF THE SIGNS

100 unit structure
10 block copolymer
11 cationic polyamino acid segment
12 spatial extent of hydrophilic polymer chain segment
20 nucleic acid

---

The invention claimed is:

1. A unit structure, consisting of:
   a single double-stranded nucleic acid having 18 to 30 base pairs, and
   two block copolymers, each having a cationic polyamino acid segment and a 2-arm branched hydrophilic polymer chain segment,
   wherein:
   (i) a difference between a total of positive charges derived from cationic groups of the cationic polyamino acid segments and a total of negative charges derived from the nucleic acid in the unit structure falls within a range of ±10% of the total of the negative charges derived from the nucleic acid,
   (ii) the 2-arm branched hydrophilic polymer chain segment comprises two polyethylene glycol chains, each polyethylene glycol chain having a molecular weight of 20,000 Da or more,
   (iii) each of the polyethylene glycol chains has a radius of inertia (Rg) equal to or longer than half the length of the nucleic acid, and
   (iv) the cationic polyamino acid segments are bound to the nucleic acid via electrostatic bonds.

2. The unit structure according to claim 1, wherein all cationic amino acids in the cationic polyamino acid segment have only one cationic group in each side chain.

3. The unit structure according to claim 1, wherein the cationic polyamino acid segment contains exclusively cationic amino acid residues.

4. The unit structure according to claim 1, wherein the nucleic acid is siRNA.

5. The unit structure according to claim 4, wherein the polyamino acid chain segment of each block copolymer contains a number of positive charges that is at least approximately one-half of the total of the negative charges derived from the nucleic acid.

6. The unit structure according to claim 4, wherein each of the polyethylene glycol chains has a molecular weight of 20,000 Da to 60,000 Da.

7. A unit structure, consisting of one siRNA and two block copolymers, wherein
   (i) each block copolymer has a cationic polyamino acid segment and a 2-arm branched polyethylene glycol segment at one terminal of the polyamino acid chain segment,
   (ii) each of the arms of the polyethylene glycol has a molecular weight of from 20,000 Da to 80,000 Da, (iii) a difference between a total of positive charges derived from cationic groups of the cationic polyamino acid segments and a total of negative charges derived from the siRNA in the unit structure falls within a range of ±10% of the total of the negative charges derived from the siRNA, and (iv) the cationic polyamino acid segments are bound to the siRNA via electrostatic bonds.

8. The unit structure according to claim 7, wherein all cationic amino acids in the cationic polyamino acid segment have only one cationic group in each side chain.

9. The unit structure according to claim 7, wherein the cationic polyamino acid segment contains exclusively cationic amino acid residues.

10. The unit structure according to claim 7, wherein the two block copolymers are each selected from the group consisting of the following formulae (1)-(2):

atoms, or an unsubstituted or substituted linear or branched alkyl-substituted imino group having 1 to 12 carbon atoms;

$R^{4a}$ and $R^{4b}$ are each independently a methylene group or an ethylene group;

$R^{5a}$ and $R^{5b}$ are the same group or different groups selected from the group consisting of:

—NH—(CH$_2$)$_{p1}$—[NH—(CH$_2$)$_{q1}$—]$_{r1}$NH$_2$  (i);

—NH—(CH$_2$)$_{p2}$—N[—(CH$_2$)$_{q2}$—NH$_2$]$_2$  (ii);

—NH—(CH$_2$)$_{p3}$—N{[—(CH$_2$)$_{q3}$—NH$_2$][—(CH$_2$)$_{q4}$—NH—]$_{r2}$H}  (iii); and —NH—(CH$_2$)$_{p4}$—N{—(CH$_2$)$_{q5}$—N[—(CH2)$_{q6}$-NH$_2$]$_2$}$_2$  (iv), where p1 to p4, q1 to 6, and r1 to 2 are each independently an integer of from 1 to 5;

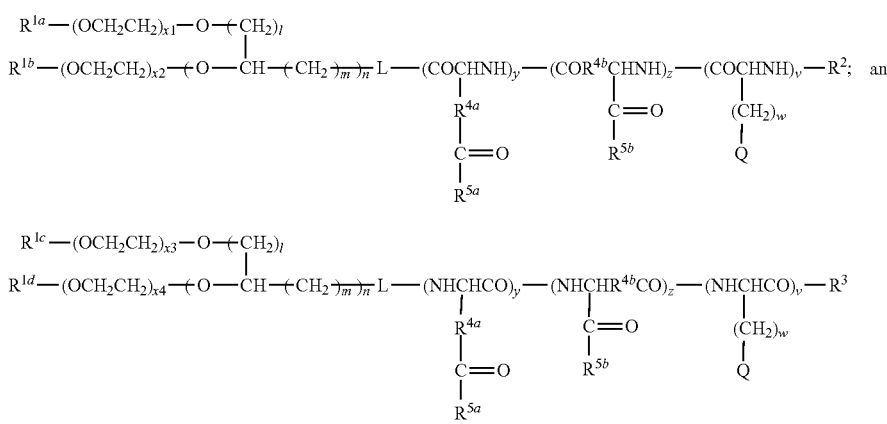

wherein:

$R^{1a}$ to $R^{1d}$ are each independently a hydrogen atom, an unsubstituted or substituted linear or branched alkyl group having 1 to 12 carbon atoms, or a group represented by the following formula (I):

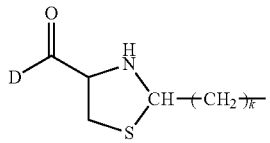

where k represents an integer of from 1 to 5, and D represents a target binding site;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^3$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon Q is —NH$_2$, —NHC(=NH)NH$_2$, or a group represented by the following formula (II);

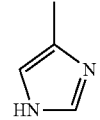

L is a divalent linking group or a valence bond;
x1 to x4 are each independently an integer of from 454 to 1818;
y, z, and v are each independently an integer of from 0 to 30, provided that y, z, and v satisfy the relationship 18≤y+z+v≤30;
w is an integer of from 1 to 6;
l and m are each independently an integer of from 0 to 5; and
n is 1.

11. The unit structure according to claim 10, wherein x1 to x4 are each independently an integer of from 454 to 1200.

12. The unit structure according to claim 11, wherein:
the siRNA is a double-stranded RNA having 21 base pairs and
y, z, and v are selected such that the number of cationic groups in the cationic polyamino acid segment is an integer of from 18 to 22.

13. A method of treating cancer, comprising:
administering a therapeutically effective amount of the unit structure according to claim 1 to a patient in need thereof.

14. A method of treating cancer, comprising:
administering a therapeutically effective amount of the unit structure according to claim 7 to a patient in need thereof.

15. The unit structure according to claim 1, each polyethylene glycol chain has a molecular weight of from 30,000 Da to 60,000 Da.

16. The unit structure according to claim 7, each strand of the polyethylene glycol has a molecular weight of from 30,000 Da to 60,000 Da.

* * * * *